United States Patent
Huang

(10) Patent No.: US 8,507,562 B2
(45) Date of Patent: Aug. 13, 2013

(54) SYNTHESIS OF (1)-BETA-ELEMENE, (−)-BETA-ELEMENAL, (−)-BETA-ELEMENOL, (−)-BETA-ELEMENE FLUORIDE AND THEIR ANALOGUES, INTERMEDIATES, AND COMPOSITION AND USES THEREOF

(75) Inventor: Lan Huang, Bronx, NY (US)

(73) Assignee: HYWE Pharmaceuticals, Inc., Berkeley Heights, NJ (US)

( * ) Notice: Subject to any disclaimer, the term of this patent is extended or adjusted under 35 U.S.C. 154(b) by 816 days.

(21) Appl. No.: 11/649,558

(22) Filed: Jan. 4, 2007

(65) Prior Publication Data

US 2007/0135526 A1 Jun. 14, 2007

Related U.S. Application Data

(63) Continuation of application No. PCT/US2005/014699, filed on May 2, 2005, which is a continuation of application No. 10/886,334, filed on Jul. 7, 2004.

(60) Provisional application No. 60/661,790, filed on Mar. 15, 2005.

(51) Int. Cl.
   *A61K 31/11* (2006.01)
   *A61K 31/045* (2006.01)
   *A61K 31/025* (2006.01)
   *A61K 31/015* (2006.01)

(52) U.S. Cl.
   USPC ............ 514/693; 514/729; 514/747; 514/763

(58) Field of Classification Search
   USPC ............ 203/73, 39, 71; 424/766, 725, 93.21; 514/274
   See application file for complete search history.

(56) References Cited

U.S. PATENT DOCUMENTS 6,464,839 B1 * 10/2002 Chen et al. .................... 203/73
6,599,909 B1 * 7/2003 Buchsbaum et al. ......... 514/274

FOREIGN PATENT DOCUMENTS

JP 08027050 * 1/1996

OTHER PUBLICATIONS

Corey et al., J. Am. Chem. Soc., vol. 117, No. 1, 1995.*
Maurer et al., Helvetica Chimica Acta, 60(7), 1977, pp. 2177-2190, (abstract only).*

* cited by examiner

*Primary Examiner* — Kamal Saeed
(74) *Attorney, Agent, or Firm* — Gottlieb, Rackman & Reisman, P.C.

(57) ABSTRACT

The present invention provides convergent processes for preparing (−)-beta-elemene, (−)-beta-elemenal, (−)-beta-elemenol, and (−)-beta-elemene fluoride and analogues thereof. Also provided are intermediates useful for preparing (−)-beta-elemene. The present invention further provides novel compositions based on analogues of (−)-beta-elemene, (−)-beta-elemenal, (−)-beta-elemenol, (−)-beta-elemene fluoride and methods for the treatment of cancer, such as brain tumor, lung cancer, breast cancer, prostate cancer, ovarian cancer, colorectal cancer, gastric intestional cancer, and stomach cancer.

The inventors propose a combination therapy using 1) one or more of the following anti-cancer agents: including, but not limited to, Cisplatin, 5-FU, Taxol, Taxol derivatives, and any anti-cancer agent, and 2) one or more of the following (−)-beta-elemene and its analogs, including (−)-beta-elemene, (−)-beta-elemenal, (−)-beta-elemenol, (−)-beta-elemene fluoride, and their analogs, and (−)-beta-elemene's intermediate in its chemical synthesis, for the treatment of cancer, especially for the treatment of brain tumor, lung cancer, ovarian cancer, bladder cancer, cervical cancer, colon cancer, breast cancer, and prostate cancer.

18 Claims, 5 Drawing Sheets

FIG. 1 Two different synthetic schemes of (-)-beta-elemene.
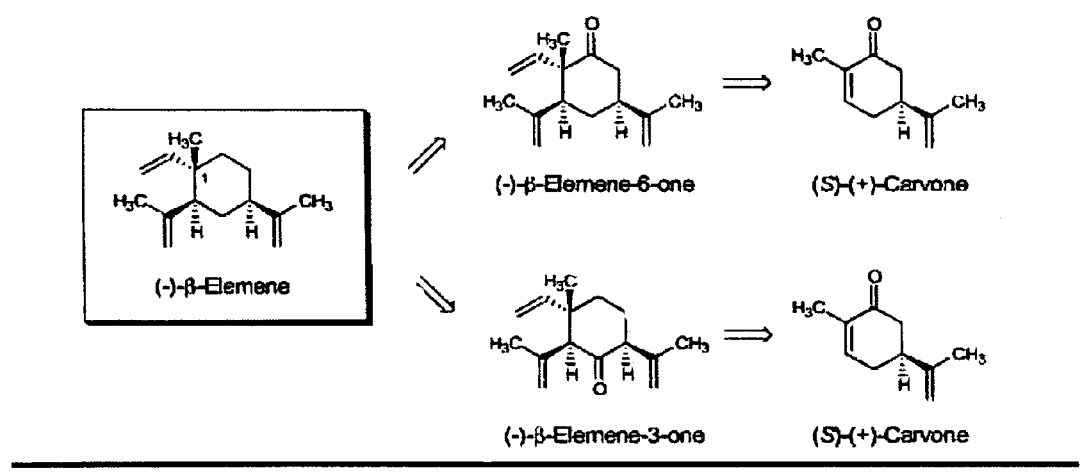
FIG. 2 Claims of elemene-like structures or derivatives or analogs.
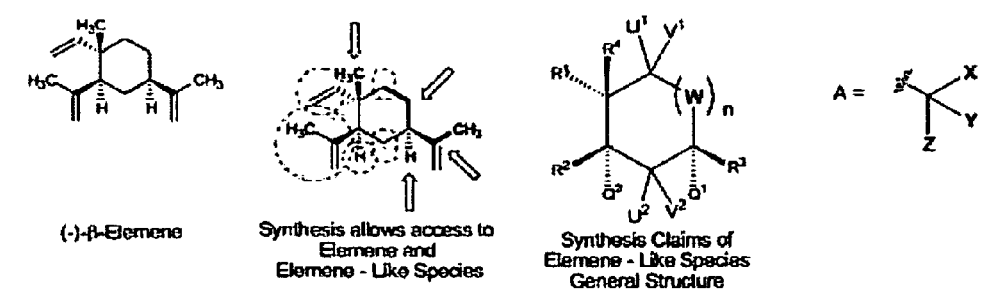

FIG. 3 Detailed description of two de novo synthesis routes of (-)-beta-elemene from (S)-(+)-Carvone.
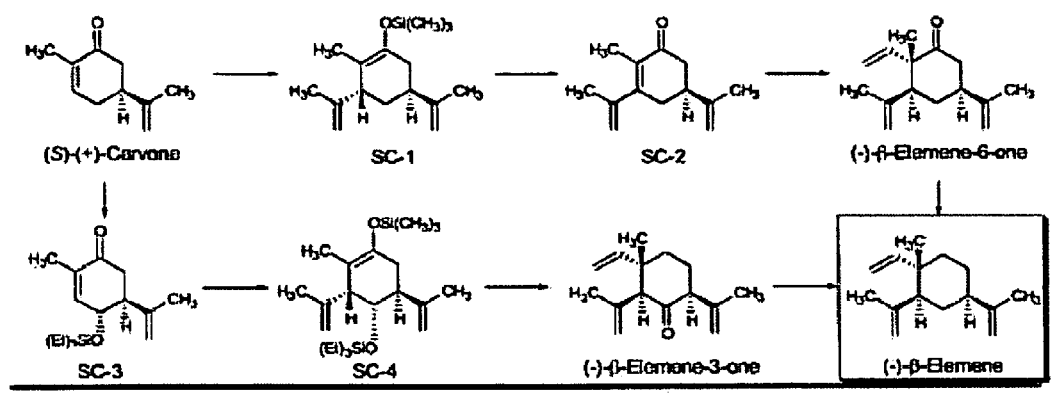
FIG. 4 Corey Synthesis analysis for (-)-beta-elemene.
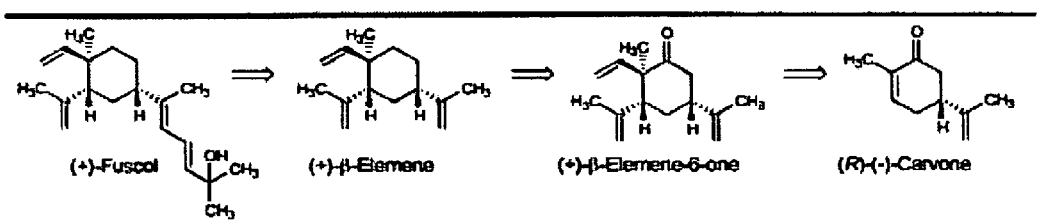

FIG. 5 Preparation of elemene derivative (+)-Fuscol from (R)-(-)-Carvone.
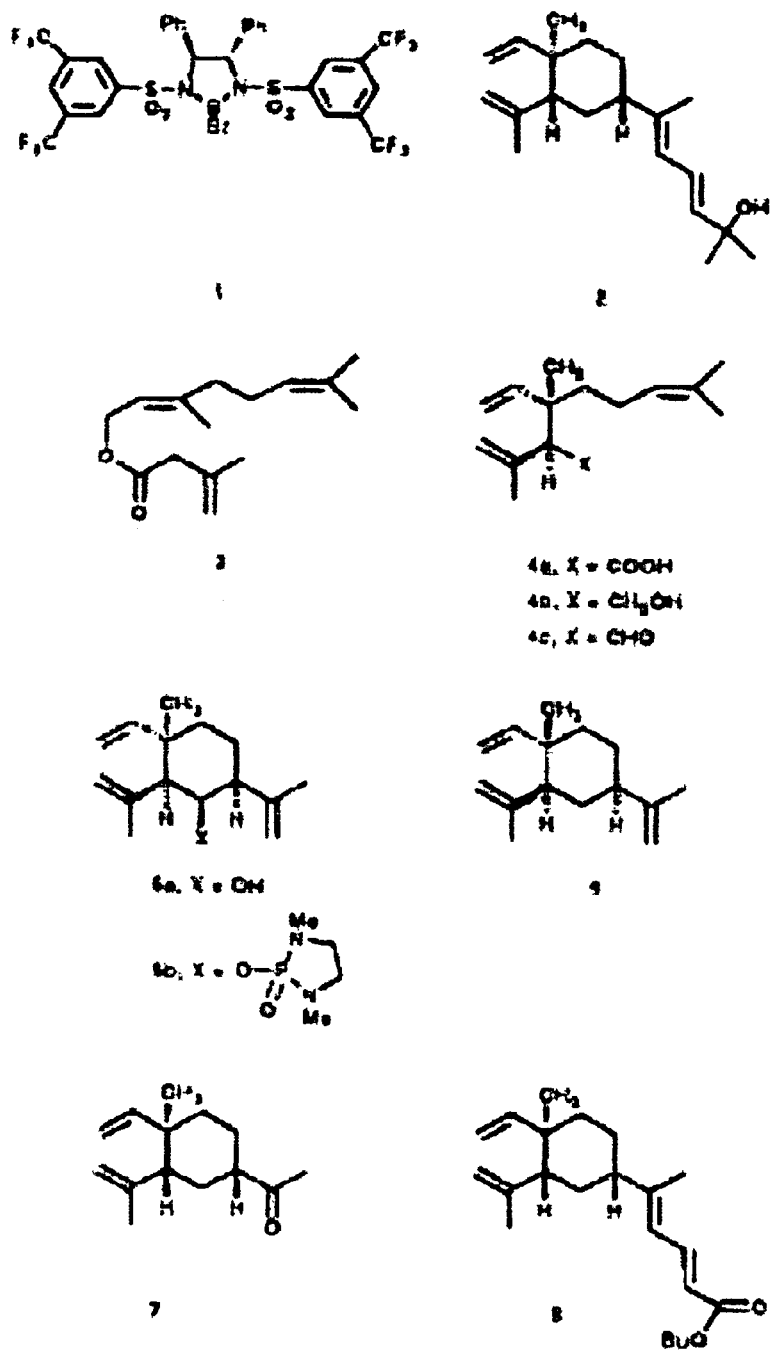

FIG. 6 Structures of ten (-)-beta-elemene derivatives synthesized.
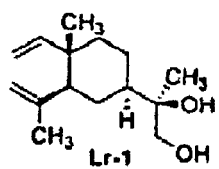
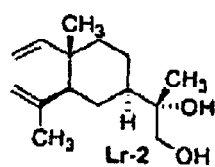
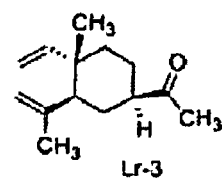
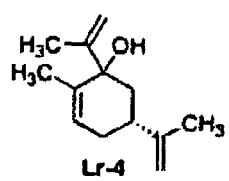
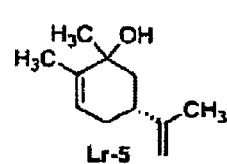
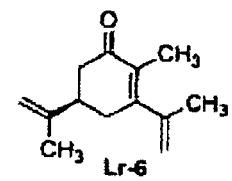
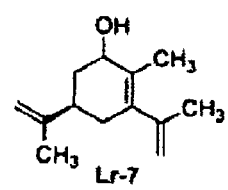
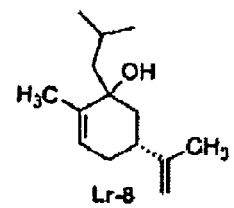
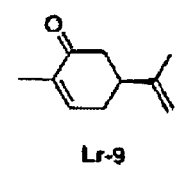
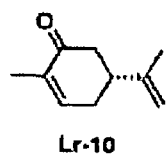

FIG. 7 Chemical structures of β, γ, δ-elemene
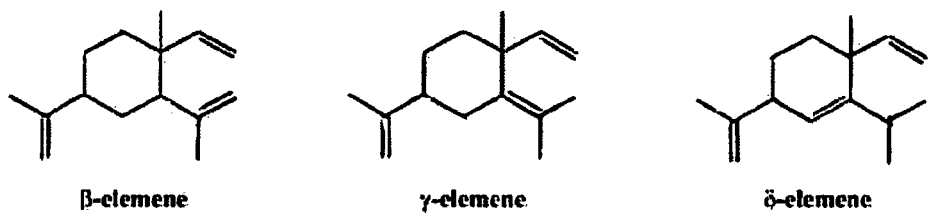
β-elemene    γ-elemene    δ-elemene
FIG 8 Chemical structures of (-)-beta-elemene derivative and (-)-beta-elemene like structures (GENUS #1).
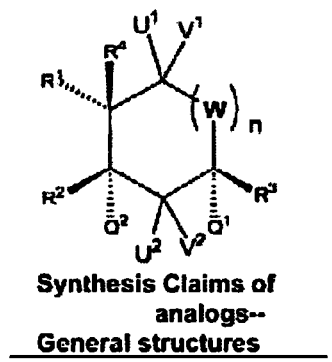
Synthesis Claims of analogs--
General structures
FIG. 9 Claims of elemenol, elemenal, and elemene fluoride analog structures
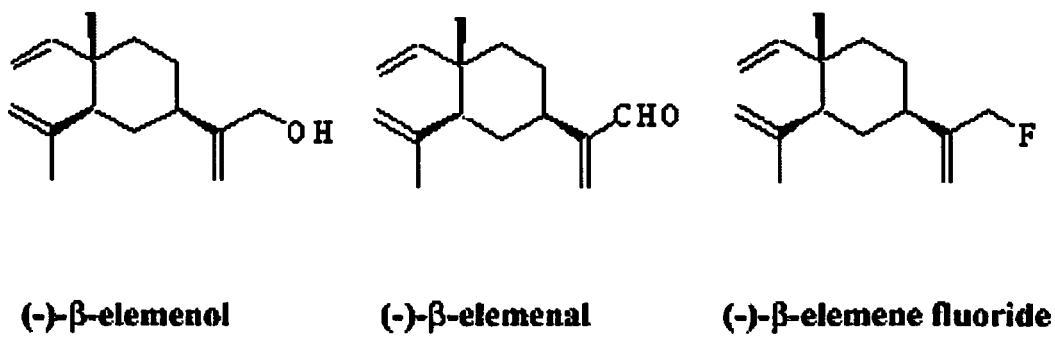
(-)-β-elemenol    (-)-β-elemenal    (-)-β-elemene fluoride

SYNTHESIS OF (1)-BETA-ELEMENE, (-)-BETA-ELEMENAL, (-)-BETA-ELEMENOL, (-)-BETA-ELEMENE FLUORIDE AND THEIR ANALOGUES, INTERMEDIATES, AND COMPOSITION AND USES THEREOF

CROSS-REFERENCE TO RELATED APPLICATIONS

This application is a continuation of prior co-pending PCT International Application No. PCT/US2005/014699, filed on May 2, 2005, which (1) was a continuation of prior U.S. patent application Ser. No. 10/886,334, filed Jul. 7, 2004, now abandoned, and (2) also claimed the benefit of prior U.S. Provisional Patent Application Ser. No. 60/661,790, filed Mar. 15, 2005.

DESCRIPTION

1. Field of the Invention

The present invention is in the field of elemene analogs and elemenal analogues. In particular, the present invention relates to processes for the preparation of (-)-beta-elemene, (-)-beta-elemenal (a (-)-beta-elemene metabolite in mammals), (-)-beta-elemenol, (-)-beta-elemene fluoride and their analogs, which are useful as non-cytotoxic anticancer therapeutics, and their effects in anti-MDR effects. The composition and usage of (-)-beta-elemene, (-)-beta-elemenal, (-)-beta-elemenol, (-)-beta-elemene fluoride and their analogs, and intermediates for preparing (-)-beta-elemene are protected.

The invention is applicable to cancers generally in mammals and the reference to human biochemistry is not intended to be limiting, but illustrative. The term patient or body or reference to humans is utilized for convenience, but includes all mammalian patients or bodies.

2. Background of the Invention

I. Anti-cancer Efficacy of Elemene Mixture

Elemene mixture (mixture of β (beta), γ (gamma), δ (delta)-elemene, main component is the beta-form) is a mixture of naturally occurring compounds that can be isolated from many sources including *G. Cymbopogon* winterianus Jowitt, *Zhangzhou Aglaia odorata* flower, *Fuzhou Aglaia odorata* flower, *Chunging Aglaia odorata* flower, *Chunging Aglia odorata* leaves, *Zhangzhou Aglaia odorata* leaves, *Yibin geranium* leaves, *Kunmin geranium* leaves, *Litchi chenensis cinnamomifolium*, dry *Lauris nobilis*, *Citrus limona* leaves, *Vitis vinifera* grape leaves, *Clausena lansium* leaves, *Fortunella margarita* leaves, *Fortunella odorata*, C. Wenyunjin Chen, and *Magnolia sieboldi*. It was first extracted in 1954 (Herout, V., Motl, O., Sorm, F., Coll. Czech. Chem. Commun 1954, 19, 990). In China starting from 1983 Elemene mixture was in development for anti-cancer treatment. Elemene drug is a mixture of Elemene isomers, with the beta form as its major component.

In 1993, Elemene mixture emulsion (0.5%, total β, γ, δ-elemene at 65% pure in the drug composition) was approved in China to treat pleural fluid caused by lung cancer. After the approval in 1993, Elemene mixture emulsion (0.5%, 65% pure) was shown to be effective in many off-label indications, treating over 10,000 cancer patients and its efficacy/safety profiles are well documented in the Chinese medical literature. The cancer indications include lung cancer, liver cancer, colon cancer, breast cancer, prostate cancer and others.

The therapeutic properties of Elemene mixture are not understood. Indeed, it is unknown whether one or all of the major components are necessary for activity or whether a minor isomer, or enantiomer, of one of these components is active. In our studies, animal tests suggested that 98% pure of (-)-beta-elemene exhibits similar clinical effects as that of Elemene mixture (2% injection, 85% pure).

In our invention, we discovered for the first time that major active component was (-)-beta-elemene ($C_{15}H_{24}$, M.W. 200.4), which can additionally pass the blood-brain-barrier, ideal to treat brain tumor patients.

II. Molecular Mechanism

1) Mechanism of Elemene Mixture (0.5% Emulsion, 65% Pure)

Elemene mixture (65% pure) appears to inhibit cancer cell growth/division, through blocking cell cycle transition from G0/G1 phase to S phase (Xu, X. J. et al. Studies of β-Elemene's induction of human liver cancer cells, Chinese Journal of Clinical Oncology, Jul. 30-32, 1999). According to flow cytometry data (Elemene at 20 ug/ml, liver cancer cell SMMC), Elemene appeared to block the G0/G1 to S phase transition.

Immunocytochemistry data indicated that Elemene mixture induced tumor suppresser p53's expression, which potentially leads to inhibition of G0/G1 to S phase transition for DNA repair (Xu, X. J. et al. Studies of β-Elemene's induction of human liver cancer cells, Chinese Journal of Clinical Oncology, Jul. 30-32, 1999).

Elemene mixture induces apoptosis in human liver cancer cells at a dose and time dependent manner, according to electron microscopy and DNA fragmentation data (Xu, X. J. et al. Studies of β-Elemene's induction of human liver cancer cells, Chinese Journal of Clinical Oncology, Jul. 30-32, 1999). Elemene mixture also induces apoptosis and down-regulates expression of Bcl-2 protein in human leukemia K562 cells (Yuan. J et al. Elemene induces apoptosis and regulates expression of bcl-2 protein in human leukemia K562 cells, Zhongguo Yao Li Xue Bao (Chinese Pharmacology Journal), 20: 103-106, 1999). Elemene mixture induces differentiation of lung tumor cells (Aip-937, A549, SPC-A1, small cell lung cancer H128) (Qian, J. et al. The studies of Elemene Emulsion on the Reversion of human lung cancer cells, Chinese Journal of Clinical Oncology, Jul. 7-10, 1999), melanoma cells B16 (Qiang, j. Et al. The induction of Differentiation of B16 cells by Elemene Emulsion, Chinese Journal of Clinical Oncology, Jul. 16-19, 1999). The ultrastructure showed the morphological changes, such as microvilli decrement and nucleus pyknosis.

Apoptosis induced by Elemene mixture might be due to an effect on protein expression levels: decrease of Bcl-2 and c-myc, and elevation of p53. Bcl-2 inhibits apoptosis. Bcl-2 protein is not expressed in normal liver cells, and its high expression could lead to tumor cell's survival. C-myc is a signaling protein, preceding signal transduction pathways. C-Myc potentially induces cell division. P53, a hallmark tumor suppresser is especially linked to apoptosis. When DNA is damaged in cells, p53 protein levels increase to inhibit G0/G1 to S transition for DNA repair. Prolonged arrest induced by elevated level of p53 induces apoptosis.

Overall, Elemene mixture (65% pure) is different from other cytotoxic cancer drugs, with high $IC_{50}$ for tumor cells (at 20-50 ug/ml in vitro). Its clinical tumor shrinkage effect appears to be due to this mixture's ability to induce apoptosis, inhibit cell cycle, and induce differentiation. However, the active component is unknown before our discovery.

2) Mechanism of (-)-Beta-elemene (98% Pure)

We have identified for the first time that the active component in the Elemene mixture is (-)-beta-elemene. We also have conducted in vitro experiment to elucidate (-)-beta-elemene's molecular mechanism in its anti-cancer effect.

(−)-beta-elemene had differential inhibitory effects on cell growth between Non-small-cell lung cancer (NSCLC) cell lines and lung fibroblast and bronchial epithelial cell lines. In addition, (−)-beta-elemene was found-to arrest NSCLC cells at cell cycle G2-M phase, the arrest being accompanied by decreases in the levels of cyclin B1 and phosphor-Cdc2 (Thr-161) and increase in the levels of p27$^{kip1}$ and phosphor-Cdc2 (Tyr-15). And (−)-beta-elemene reduced the expression of Cdc25C, which dephosphorylates/activates Cdc2, but enhanced the expression of the checkpoint kinase, Chk2, which phosphorylates/inactives Cdc25C. These findings suggest that the effect of (−)-beta-elemene on G2-M arrest in NSCLC cells is mediated partly by a Chk2-dependent mechanism. In addition, (−)-beta-elemene triggered apoptosis in NSCLC cells. Results clearly show that (−)-beta-elemene induced caspase-3, -7, -9 activities, decreased Bcl-2 expression, caused cytochrome c release and increased the levels of cleaved caspase-9 and poly(ADP-ribose polymerase) in NSCLC cells. These data indicate that the effect of (−)-beta-elemene on lung cancer death may be through a mitochondrial release of the cytochrome c-mediated apoptotic pathway (Wang, G. et al. Antitumor effect of (−)-beta-elemene in non-small-cell lung cancer cells is mediated via induction of cell cycle arrest and apoptotic cell death, Cell. Mol. Life. Sci., 62 (2005), in press).

3) Anti-MDR Effect of Beta-elemene

Elemene does not produce Multi-drug Resistance (MDR) effect (Wang, B. C. et al. The Experimental Studies of Association between Elemene and Tumor Multidrug Resistance, Chinese Journal of Clinical Oncology, Jul. 10-13, 1999). Human hepatic cancer BEL-7402 cell line was cultured and its drug-resistance strain BEL-7402/DOX was established. After 6 weeks of induction with Elemene at 48.9 ug/ml, drug resistant BEL-7402 cells still did not express MDR1 mRNA or P-glycoprotein (P-gp). Thus drug-resistant tumor cells are sensitive to Elemene.

Accordingly, the present inventors undertook the total synthesis of (−)-beta-elemene, and as a result, have developed efficient processes for (−)-beta-elemene, as well as derivatives thereof. Each of the enclosed method is inadequate for the purpose of obtaining (−)-beta-elemene. The present invention also provides novel intermediates useful in the synthesis of (−)-beta-elemene and analogs thereof, compositions derived from such (−)-beta-elemene and analogs, purified compounds of (−)-beta-elemene and analogs, in addition to methods of use of the (−)-beta-elemene and (−)-beta-elemene analogs in the treatment of cancer. Remarkably, (−)-beta-elemene and its derivatives of the invention have exceptionally high specificity as anti-tumor agents in vivo, and are more effective for cancer treatment, and less toxic to normal cells than the principal chemotherapeutics currently in use, including taxol, vinblastin, adriamycin and camptothecin.

III. Brain Tumor Field's Need of New Drugs

1) Brain Tumor Introduction

The development of new effective brain tumor therapies is lagged behind compared to the treatment of other malignancies, with prognoses and mortality rates similar to those from 30 years ago. Malignant gliomas, the most common subtype of primary brain tumors, are aggressive, highly invasive, and neurologically destructive tumors. Its most aggressive manifestation is glioblastoma, with median survival ranges from 9 to 12 months, despite maximum treatment efforts.

15,000 brain tumor cases are reported each year in the United States. Since more than 50% of these tumors are malignant gliomas, upwards of 7,500 new cases of glioblastoma and anaplastic astrocytoma can be expected to occur yearly. Brain tumors are the second leading cause of cancer death in children under age 15 and in young adults up to age 34. Brain tumors are the second fastest growing cause of cancer death among those over age 65. There is an urgent need to have effective glioblastoma therapy to prolong these patients' lives and improve their quality of life.

2) Brain Tumor Grade Specification

Gliomas have been defined pathologically as tumors that display histological, immunohistochemical, and ultra-structural evidence of glial differentiation. The most widely used scheme for classification and grading of gliomas is that of the World Health Organization (WHO). Gliomas are classified according to their hypothesized line of differentiation, that is, whether they display features of astrocytic, oligodendroglial, or ependymal cells. They are then graded on a scale of I to IV according to their degree of malignancy as judged by various histological features. Grade I tumors are biologically benign and can be surgically cured if deemed respectable at the time of diagnosis; grade II tumors are low-grade malignancies that may follow long clinical courses but are not curable by surgery; grade III tumors are malignant and lead to death within a few years; grade IV tumors (glioblastoma) are highly malignant, usually recalcitrant to chemotherapy, and lethal within 9-12 months.

3) Current Therapy for Brain Tumors

The major treatments consist of 1) Surgery, 2) Radiation therapy, 3) Chemotherapy, and 4) Biologic therapy. Since the brain poses a large problem for drug delivery, chemotherapy is usually co-delivered with a blood-barrier blocker (eg. mannitol). Over 50% of patients seek alternative therapies in addition to conventional treatment. Current chemotherapy in US include the following:

1) Anti-angiogenesis agents cuts off the blood supply of tumors. These agents currently or soon to be under investigation include thalidomide, TNP-470, platelet factor 4 (PF4), interferon and angiostatin.
2) Differentiating Agents are classes of drugs that can convert immature dividing tumor cells into mature cells, stopping tumor growth. Examples include retinoic acid, phenylacetate, and bryostatin.
3) Immunotherapy aims to make the immune system more effective in seeking out and destroying cancerous cells. Currently under investigation are several tools considered useful for boosting the immune system: Interferon, lymphocytes, and tumor vaccines.
4) Other treatments include drugs as follows: CPT-11, PCV, Tamoxifen, Thalidomide, VP-16/Etoposide, and BCNU. Adjuvant chemotherapy, usually with BCNU (1,3-bis (2-chlorethyl)-1-nitrosourea), increases survival slightly. Attempts to administer BCNU by arterial injection have been complicated by irreversible encephalopathy and ipsilateral visual loss owing to retinal toxicity.

Currently the most exciting chemotherapy drug for brain tumor is TEMODAR, which was approved by the US Food and Drug Administration (FDA) in August 1999 for adult patients with recurrent anaplastic astrocytoma. TEMODAR (temozolomide) is the first oral chemotherapeutic agent found to cross the blood-brain barrier. This oral, cytotoxic alkylating agent is the leader in a new class of compounds known as imidazotetrazines. The overall tumor response rate to TEMODAR was 22 percent, including complete responses (9 percent) and partial responses (13 percent). A complete response (CR) is defined as the loss of the tumor for at least two consecutive months as measured by MRI. A decrease of more than 50 percent in the tumor area for two months defined a partial response (PR).

4) Efficacy of Elemene Mixture to Treat Brain Tumors

Elemene passes the blood brain barrier (BBB) (Qian, J., New anti-tumor drug, Elemene's pharmacology and Clinical results, Chinese Journal of Clinical Oncology, Jul. 1-3, 1999). $^3$H labeled Elemene was injected intravenously into or taken orally by experimental animals. Radioactivity was detected in animals' brain.

Elemene mixture injection (2% injection, 85% pure) is pending approval by the Chinese FDA to treat primary and secondary brain tumor patients. This formulation has passed the approval of the drug technical review board in China. In the clinical trial conducted in China, this new formulation of Elemene mixture (2% injection, 85% pure), which contains the same Active Pharmaceutical Ingredient (API), but different non-active components to stabilize Elemene in a clear solution was tested. In a 61 patient trial, Elemene mixture (2% injection, 85% pure) is better than the available drugs (including TEMODAR, BCNU and CCNU) on the market for brain tumor patients, with tumor shrinkage effect (CR+PR) in 35-40% of the patient group. Drug TEMODAR has a CR+PR rate of 20%. CR denotes complete response, with tumor shrinking to undetectable after treatment; PR denotes partial response, with tumor shrinkage over 50% compared with tumor size before treatment. The longest survival time of a glioblastoma patient is 62 months after treatment with Elemene mixture (2% injection, 85% pure).

IV. Beta-elemenal as a Beta-elemene's Metabolite

In Li, Z. et al's paper, the Dalian group studied the metabolite of beta-elemene (98% pure, mainly beta-elemene) in the bile of rat. After i.v. 100 mg.kg-1 beta-elemene (98% pure), the metabolite in rat bile was extracted by ether. Mass spectrometry, nuclear magnetic resonance, infrared spectrometry and ultraviolet spectrometry were used to analyze the metabolite of i.v. beta-elemene in rat bile. It was suggested by nuclear magnetic resonance that the methyl of No. 11 carbon connecting with No. 10 carbon of a metabolite in rat bile was oxidized to be an aldehyde. The molecular weight of the metabolite was 218 which detected by mass spectrometry. Infrared spectrometry and ultraviolet spectrometry proved that the aldehyde existed in the metabolite. The structure of the metabolite in bile of rat was surmized to be derived from beta-elemene, possibly beta-elemenal. Thus the biotransformation of beta-elemene appears to exist in vivo.

However, in the publication above, authors did not differentiate which stereo enantiomer of elemenal was detected. And they did not further look into the activity and usage of Elemenal.

According to our animal experiment data, tritium labeled beta-elemene and its derivatives and/or its metabolites can pass blood brain barrier (BBB). But no careful experiments were done to figure out if it is beta-elemene itself, or its derivatives, or its metabolite or a combination of the above, which pass the BBB. Thus how Elemene works to treat brain tumor is unknown.

V. Multi-drug Resistance of Traditional Chemotherapy Drugs

1) Effects of Traditional Chemotherapy Drugs

Cisplatin, 5-FU, Taxol, and Taxol derivatives are traditional effective chemotherapy drugs, yet their usefulness is impaired by their multi-drug resistance, and their potential cyto-toxicity.

Cisplatin is a well-established cancer drug. Cisplatin was first synthesized in 1845, but its cytotoxic properties were not described until 1965. An experiment had been set up to see if an electric current would inhibit the reproduction of E. coli bacteria. The conclusion of the experiment was that electrolysis products from the platinum electrode were responsible for the inhibition. Cisplatin entered into clinical trials in 1971.

Cisplatin is an inorganic complex formed by an atom of platinum surrounded by chloride and ammonia atoms in the cis position of a horizontal plane. Intracellularly, water displaces the chloride to form highly reactive charged platinum complexes. These complexes inhibit DNA through covalent binding leading to intrastrand, interstrand, and protein cross-linking of DNA. Experimental and clinical data suggest that cisplatin enhances radiation therapy effects. Early studies suggested that cisplatin was cell cycle phase-nonspecific, while more recent studies have shown complex and variable effects on the cell cycle.

Cisplatin's main uses are against bladder cancer, non-small cell lung cancer, ovarian cancer, and testicular cancer. Other cancers cisplatin can treatment include adrenocortical cancer, brain tumors, breast cancer, cervical cancer, endometrical cancer, gastrointestinal cancer, germ cell tumors, gynecological sarcoma, head and neck cancer, hepatoblastoma, malignant melanoma, neuroblastoma, non-hodgkin's lymphoma, osteosarcoma, and thyroid cancer.

Taxol and 5FU are both effective anti-cancer drugs, yet they also induce MDR effects. Taxol is first discovered at the turn of last century, but the clinical trial of this drug started in 1983. Taxol works on mitotic check point in the cell cycle. Taxol is mainly used in breast cancer, ovarian cancer, head and neck cancer, and lung cancer. 5FU was developed in 1957 based on the observation that tumor cells utilized the base pair uracil for DNA synthesis more efficiently than did normal cells of the intestinal mucosa. It is a fluorinated pyrimidine that is metabolized intracellularly to its active form, fluodeoxyuridine monophophate (FdUMP). The active form inhibits DNA synthesis by ihibiting the normal production of thymidine. 5FU is cell cycle phase specific (S-phase). 5FU is mainly used in breast cancer, colorectal cancer, gastric cancer, and hepatic cancer. 5FU's less frequent uses include actinic keratosis, bladder cancer, cervical cancer, endometrial cancer, head and neck cancer, non-small cell lung cancer, ovarian cancer, pancreatic cancer, and prostate cancer.

2) MDR Effect of Cancer Cells

MDR effect of cancer cells is one major reason for the failure of many chemotherapeutic drugs. After cancer cells experience chemotherapeutic drug A, these cancer cells are not only resistant to drug A, but also resistant to drugs with different chemical structure, function, or inhibition mechanism from drug A. To date, overexpression of P170 glycoprotein on cell membrane is one of the main reasons causing MDR. P170 glycoprotein is a pump that is dependent on energy. P170 pumps out drugs from inside cells so that the cells could lower drug concentration inside cells—defined as MDR effect. So far scientists have discovered many MDR reversion drugs, summed up as follows: 1) calcium channel blockers, 2) calmodulin inhibitors, 3) Steroids and hormones, 4) immune modulators, 5) antibiotics. The above MDR reversion agents are effective in in vitro experiments, but are too toxic for human trials.

Cisplatin induces P-glycoprotein's expression. According to Yang et al's report, p-glycoprotein was expressed in ovarian cancer cell line following treatment with cisplatin (Yang, X, and Page, M, P-glycoprotein expression in ovarian cancer cell line following treatment with cisplatin, Oncol. Res. 1995, 7(12): 619-24). Human ovarian cancer cell line SKOV3 was grown during a period of four months in the presence of increasing concentrations of cisplatin (25-100 ng/ml). In the course of this treatment, the cells exhibited dramatic morphology changes, including reduction in cell size, loss of cellular projections and clustering. This was accompanied by the appearance of p-glycoprotein on the cell membrane. The new cell, designated SKOV3/CIS, acquired resistance to classical MDR drugs, such as doxorubicin, taxol, and actinomycine D. Verapamil enhanced the sensitivity of SKOV3/CIS to doxorubicin (260-fold), in conformity with the proposed mechanism of p-glycoprotein in MDR, but it did not potentate cisplatin cytotoxicity in SKOV3/CIS cells.

Certain drugs have been shown to reduce Cisplatin's MDR effect. In literature, SDZ PSC 833, a semisynthetic undecapeptide derived from cyclosporine D, is one of the most potent known inhibitors of the multidrug transporter P-glycoprotein (Baekelandt, M et al., Phase I/II trial of cisplatin and doxorubicin with SDZ PSC 833 in patients with refractory ovarian cancer, Proc. Annu. Meet. Am. Soc. Clin. Oncol 1997; 16: A757). Patients with histologically verified ovarian cancer were eligible if they had clinically resistant disease, defined as either stable disease after at least 3 cycles or disease progression after at least 2 cycles while treated with a combination of cisplatin and an anthracyclin. Treatment was then continued with Cisplatin 50 mg/m2 and doxorubicin with the addition of PSC. The maximal tolerated dose for doxorubicin was determined to be 35 mg/m2 with PSC. By administering SDZ PSC 833 intravenously together with cisplatin and doxorubicin, the clinicians observe major response in heavily pretreated patients with progress disease, and acceptable toxicity.

The application of MDR-reversing agents is a potential principle means that conquers clinical drug resistance and improves the effect of chemotherapy. For nearly two decades, although many reversing compounds have been identified, clinical application of these agents is confined for their toxic and side effects.

We are the first inventors discovering that (−)-beta-Elemene can reverse the MDR effects of Cisplatin, 5-FU, or Taxol (or Taxol derivatives). (−)-beta-elemene or its analogs could be used as a combination therapy agent with Cisplatin, 5-FU, or Taxol (or Taxol derivatives), because it is a non-cytotoxic anticancer drug. Clinical trials have demonstrated that beta-elemene emulsion mixture (majority active ingredient is (−)-beta-elemene) exhibits no detriment to heart, liver, or kidney, and no inhibitory effect on bone marrow.

SUMMARY OF THE INVENTION

In the Following Paragraphs, (−)-Beta-elemenal, (−)-Beta-elemenol, and (−)-Beta-elemene Fluoride are all Analogs of (−)-beta-elemene.

1) One object of the present invention is to provide processes for the preparation of (−)-beta-elemene and its analogs useful as anticancer therapeutics.
2) Another object of the present invention is to provide various compounds useful as intermediates in the preparation of (−)-beta-elemene as well as analogues thereof.
3) A further object of the present invention is to provide synthetic methods for preparing such intermediates.
4) An additional object of the invention is to provide compositions useful in the treatment of subjects suffering from cancer comprising any of the analogues of the (−)-beta-elemene available through the preparative methods of the invention optionally in combination with pharmaceutical carriers.
5) A further object of the invention is to provide methods of treating subjects suffering from cancer using any of the analogues of (−)-beta-elemene available through the preparative methods of the invention optionally in combination with pharmaceutical carriers.
6) Another object of the invention is to use (−)-beta-elemene and its analogs in a combination therapy against different cancer types with cisplatin, or Taxol (or its derivative), or 5FU. (−)-beta-elemene and its analogs are effective not only in reversing multi-drug resistance in cancer cells, both in vitro and in vivo, but have been determined to be active as collateral sensitive agents, which are more cytotoxic towards MDR cells than normal cells, and as synergistic agents, which are more active in combination with other cytotoxic agents, such as cisplatin, than the individual drugs would be alone at the same concentrations. (−)-beta-elemene or its analogs could lower cisplatin or Taxol (or its derivatives), or 5FU's IC50 to inhibit tumor grown in cancer cell lines, and they might lower cisplatin, or Taxol (or its derivative), or 5FU's intake in cancer patients, and thus lowering these cytotoxic drug's side effects.

(−)-Beta-elemenal, a Metabolite of (−)-Beta-elemene, is a More Potent Anti-cancer Agent than (−)-Beta-elemene The present inventors undertook an unambiguous synthesis of (−)-beta-elemenal, and as a result, have developed efficient processes for (−)-beta-elemenal, as well as analogs thereof. The present invention also provides novel function of (−)-beta-elemenal and analogs thereof. The usage findings are unexpected. (−)-beta-elemenal is more potent in anti-cancer activity than that of (−)-beta-elemene. Additionally, (−)-beta-elemenal, serving as a metabolite of (−)-beta-elemene, could potentially exhibit longer half life in human body, and thus simplifying the drug dosing scheme.

Other (−)-Beta-elemene Analogs

The present inventors undertook the synthesis of (−)-beta-elemenol, and as a result, have developed efficient processes for (−)-beta-elemenol, as well as analogs thereof. (−)-beta-elemenol is more soluble than (−)-beta-elemene, which has its potential advantages. (−)-beta-elemenol is as potent as (−)-beta-elemene as an anti-cancer agent.

The present inventors also undertook the synthesis of (−)-beta-elemene fluoride, a novel compound, and as a result, have developed efficient processes for (−)-beta-elemene fluoride, as well as analogs thereof. (−)-beta-elemene fluoride (with radioactive Fluoride 18) constitutes a potential imaging agent, for example, in the brain, and potential therapeutic agent in radiotherapy. (−)-beta-elemene fluoride is as potent as (−)-beta-elemene as anti-cancer agent.

BRIEF DESCRIPTION OF THE DRAWINGS

FIG. 1 Two different synthetic schemes of (−)-beta-elemene.

FIG. 2 Claims of elemene-like structures or derivatives.

FIG. 3 Detailed description of two de novo synthesis routes of (−)-beta-elemene from (S)-(+)-Carvone.

FIG. 4 Corey Synthesis analysis for (−)-beta-elemene.

FIG. 5 Preparation of elemene derivative (+)-Fuscol from (R)-(−)-Carvone.

FIG. 6 Structures of ten (−)-beta-elemene derivatives synthesized.

FIG. 7 Chemical structures of β, γ, δ-elemene

FIG. 8 Chemical structures of (−)-beta-elemene derivative and like structures (GENUS #1).

FIG. 9 Claims of elemenol, elemenal, and elemene fluoride analog structures

DETAILED DESCRIPTION OF THE INVENTION

1) Synthesis Route and Composition Claims of (−)-Beta-elemene and its Analogs

The inventors claimed the discovery of the unexpectedly efficacious, safe, non-multi drug resistant effect, non-toxic, and broadly applicable use of (−)-beta-Elemene as an anti-viral, anti-microbial, anti-biotic and especially as an anticancer chemotherapeutic; moreover, (−)-beta-Elemene analog structures are claimed (GENUS #1, as shown in FIG. 8), as are the processes by which said structures are obtained as well as the processes by which (−)-beta-Elemene is obtained. The use of (−)-beta-Elemene and (−)-beta-Elemene analogs formulated singularly or in combination for anti-viral, anti-microbial, and anti-cancer applications is also claimed.

Synthesis of (−)-beta-Elemene

It is of interest to note that (−)-beta-Elemene has not been synthesized in enantiomerically pure form. Enantiomeric purity is critical for proper evaluation of a drug. For example, Thalidimide enantiomers are either highly effective medicines or horribly disfiguring teratogens, depending on the enantiomer. Given the major impact that our recent studies of (−)-beta-Elemene formulated alone and in conjugation suggest, the inventors claim the synthesis of (−)-beta-Elemene and (−)-beta-Elemene analogs. Four synthetic plans are presented below.

Part 1: First, Two de novo Syntheses of (−)-Beta-elemene and a Wide Range of (−)-Beta-elemene-like Compounds from (S)-(+)-Carvone is Claimed. It is Anticipated That:

A) Beginning with (S)-(+)-Carvone, (−)-beta-Elemene derivative SC-1 can be readily procured by conjugate addition with a 2-propenyl unit, for example, via lithium di-2-propenyl cuprate (a Gilman reagent), and trapping of the enolate, for example with triethylsilyl chloride, to give the silyl enol ether. Conversion of SC-1 to SC-2 enables the formation of (−)-beta-Elemene-6-one is in a short sequence as follows: Oxidation of enol ether SC-1 to enone SC-2 [using palladium (II)]. Subsequent 1,4-conjugate addition with hydride, for example effected with a copper reagent, followed by trapping with methyl iodide creates the α,α-dimethyl ketone. C—H bond activation of the equatorial methyl (using, for example, the oxime derived from the ketone) can be followed by further oxidation of the resultant alcohol to the aldehyde followed by olefination giving (−)-beta-Elemene-6-one. The oxidant in C—H bond activation may be, for example, palladium (0) or platinum (II). Conversion of (−)-beta-Elemene-6-one to (−)-beta-Elemene, can be achieved by reduction (for example, hydrazine, potassium hydroxide, heat—a Wolff-Kishner reduction).

B) A second route using (S)-(+)-Carvone is oulined as well and is similar to Plan A above, however, this second route provides access to several other (−)-beta-Elemene-like molecules: Selective oxidation of (S)-(+)-Carvone at position 3 [using the (−)-beta-Elemene numbering], followed by suitable protection, if necessary, will give SC-3 (in the instance shown, protection of the 3-hydroxyl is given as the triethyl silyl ether). Following a similar course as in (A) above, SC-4 can be readily procured by conjugate addition with a 2-propenyl unit, for example, via the lithium di-2-propenyl cuprate (Gilman reagent) and trapping of the enolate as an enol ether (for example, with triethyl silyl chloride) as shown. Conversion of this adduct to (−)-beta-Elemene-3-one is outlined as follows: Oxidation of SC-4 to the enone can be achieved for example using palladium (II), followed by subsequent 1,4-conjugate addition of hydride (for example, effected with a copper reagent) followed by trapping with methyl iodide creates the a,a-dimethyl ketone. C—H bond activation of the equatorial methyl utilizing the oxime, derived from he ketone, followed by oxidation to the aldehyde and subsequent olefination of said aldehyde. The remaining carbonyl can be removed by reduction. Removal of the triethyl silyl ether to give the alcohol followed by oxidation will give (−)-beta-Elemene-3-one. Conversion of (−)-beta-Elemene-3-one to (−)-beta-Elemene can be achieved readily by reduction of the carbonyl.

Part 2: Based on Corey Synthesis (+)-Fuscol (##STR2##) of >99% Pure via the Intermediate Terpenoid (−)-Beta-elemene (##STR6##).

The reaction of geraniol with 1.1 equivalent of β, β-dimethylacryloyl chloride and 1.5 equivalent of triethylamine (CH2Cl2, −78C, 3 h) afforded the β, γ-unsaturated ester ##STR3## (99% yield) in an interesting reaction that probably proceeds via a vinylketene intermediate. Treatment of ##STR3## in toluene with 1.1 equivalent of (S,S)-bromoborane ##STR1## and 8.3 equivalent of triethylamine (−70 C for 27 h, then 4 C for 36 h) afforded the Ireland-Claisen product ##STR4a## as a major product along with a minor diastereomer (85% total yield). Reduction of the mixture to the corresponding primary alcohols (LiAlH4, Et2O, 23 C, 24 h) and chromatography on AgNO3-impregnated silica gel gave diastereomerically pure ##STR4b## (70% yield) of > 99% enantiomeric purity. Treatment of ##STR4c## with 1.1 equivalent of Et2AlCl (CH2Cl2, −78 C, 1.5 h) followed by extractive isolation and chromatography on silica gel-AgNO3 furnished the cyclized equatorial alcohol ##STR5a## (88% yield) along with 3% yield of less polar diastereomer (having equatorial hydroxyl and axial beta-isopropenyl substituents). Reaction of ##STR5a## with 2-chlorol-1,3-dimethyl-1,3,2-diazaphospholane and triethylamine (CH2Cl2, 23 C, 75 min) provided, after oxidation with 1.2 equivalent of H2O2 for 10 min, ##STR5b##, which was reduced with excess lithium and tert-amyl alcohol (4 equivalent) in liquid NH3-THF (−33 C, 10 h) to give (−)-beta-elemene (##STR6##, 95% yield), [alpha]23D-15.4 (c=0.6, CHCl3), which was indistinguishable, by NMR and infrared spectroscopic comparison, from an authentic sample of naturally derived (−)-beta-elemene.

(−)-beta-elemene (##STR6##) was converted to the methyl ketone ##STR7## by a two-step sequence. Catalytic dihydroxylation with the Sharpless phthalazine-linked bisether with dihydroquinidine, (DHQD)2-PHAL (0.1 equivalent), K2OsO4 (0.01 equivalent), K3Fe(CN)6 (3 equivalent), K2C03 (3 equivalent), and CH3SO3NH2 (1 equivalent) in 1:1 tert-butyl alcohol-water at 0 C for 11 h afforded, after chromatography on silica gel, the diol resulting from selective attack at the isopropenyl appendage (1,4-) to the angular methyl group (76% yield; 92% yield corrected for recovered ##STR6##). Cleavage of the resulting 1,2-doil with 3 equivalent of NaIO4 (4:1 THF-H20, 23 C, 30 min) gave ##STR7## in 96% yield. The highly selective attack of just one of the three double bonds of ##STR6## by Os04 under catalysis by (DHQD)2-PHAL was predicted on the basis of the mechanistic model recently proposed for the asymmetric dihydroxylation reaction. Coupling the methyl ketone ##STR7## with 20 equivalent each of (n-BuO)2POCH2CH═CHCOOn-Bu and LiOt-Bu (added in four portions, THF solution, 23 C, 48 h) furnished the tetraene ester ##STR8## (Butyl 5-[(1'S,3'R,4'R)-3'-Isopropenyl-4'-methyl-4'-vinylcyclohexyl]-(E, E)-hexadienoate)in 80% yield after chromatography on silica gel. Reaction of ##STR8## with 5 equivalent of MeLi (Et2O, −30 C, 12 h) afforded (+)-fuscol (##STR2##), $[\alpha]^{23}_D$+19.7° (c=1, CHCl1), as a colorless oil in 95% yield.

For (+)-fuscol derivatives:

As used herein, the term "linear or branched chain alkyl" encompasses, but is not limited to, methyl, ethyl, propyl, isopropyl, t-butyl, sec-butyl, cyclopentyl or cyclohexyl. The alkyl group may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido and/or N-acylamino moieties.

As used herein, the terms "alkoxycarbonyl", "acyl" and "alkoxy" encompass, but are not limited to, methoxycarbonyl, ethoxycarbonyl, propoxycarbonyl, n-butoxycarbonyl, benzyloxycarbonyl, hydroxypropylcarbonyl, aminoethoxycarbonyl, sec-butoxycarbonyl and cyclopentyloxycarbonyl. Examples of acyl groups include, but are not limited to, formyl, acetyl, propionyl, butyryl and penanoyl. Examples of alkoxy groups include, but are not limited to, methoxy, ethoxy, propoxy, n-butoxy, sec-butoxy and cyclopentyloxy.

As used herein, an "aryl" encompasses, but is not limited to, a phenyl, pyridyl, pyrryl, indolyl, naphthyl, thiophenyl or furyl group, each of which may be substituted by various groups, which include, but are not limited, acyl, aryl alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthoxy. Examples of acyloxy groups include, but are not limited to, acetoxy, propanoyloxy, butyryloxy, pentanoyloxy and hexanoyloxy.

The subject invention provides chemotherapeutic analogues of (−)-beta-elemene, including a compound having the structure: ##STR7## and ##STR8##.

For (−)-Beta-elemene Derivatives (Shown in FIG. 8, Genus #1):

wherein $Q^1$, $Q^2$, $R^1$, $R^2$, $R^3$, $R^4$, $U^1$, $U^2$, $V^1$, $V^2$, are each independently selected from the group consisting of hydrogen, methyl, ethyl, n-propyl, n-hexyl, CO.sub.2 Et, CH.sub.2 OH, (CH.sub.2).sub.3 OH., and linear or branched alkyl, substituted or unsubstituted alkoxy alkyl, substituted or unsubstituted alkoxy carbonyl, substituted or unsubstituted aryloxyalkyl, substituted or unsubstituted aroyl or benzoyl, trialkylsilyl, diarylalkylsilyl, aryldialkylsilyl, and triarylsilyl; and wherein W is selected from the group consisting of C, N, O. n is equal to a number between 1 to 5.

In one embodiment, the invention provides the compound having the structure: ##STR6##.

Advantages Over Prior Part on Synthesis Route in Part 1

In addition to being the only enantioselective synthesis of (−)-b-Elemene, this route is stereoselective and general with respect to modification of the scaffold. Unlike other syntheses, this route provides access to C1, C2, C3, C4, C5, and C6 derivatives, including the removal of the isopropenyl group at C4, and derivitization of the methyl group of C1.

Each of these is outlined below:

C1. The C1 position can be manipulated selectively in the 1,4-conjugate addition step delivering hydride to position C2 followed by alkylation. The alkylating group could be widely varied and in such case responds to R4 of the general structure shown in the Scheme. If the alkylating agent is methyl such that the a,a-ketone is produced, subsequent oxidation of the equatorial methyl corresponding to group R1 can be achieved, furthermore, manipulation of this oxidized methyl as an alcohol, a ketone, or other carbonyl derivative, as well as subsequent derivitization of such carbonyl derivatives giving rise to a wide range of R1 substituents can be readily achieved. Hence both R1 and R4 can be manipulated at will with this synthesis, both of these being on position C1.

C2. The C2 position can be manipulated selectively as well. Group R2 and Q2 on position C2 is selectively added in either of two ways. First, using synthesis route A: 1,4-conjugate addition producing structures like SC-1 and, subsequently, SC-2, installs these groups. A wide range of substituents can be introduced and manipulated in this way. This versatility is present in following path B as well; however, path B has additional versatility. (−)-b-Elemene-3-one can, in principle, be derivitized selectively at the C2 position, depending on adjacent substituents on position C4, taking advantage of carbonyl/enolate reactivity.

C3. Position C3 can be selectively derivitized using path B, for example, SC-3 and SC-4 and (−)-b-Elemene-3-one each represent modification on the C3 position; moreover, replacement of the triethyl silyloxy group of SC-3 or SC-4 or derivitization of the ketone on C3 of (−)-b-Elemene-3-one can be achieved selectively and replaced with a wide range of substituents as U2 and V2.

C4. Position C4 derivatives can be obtained readily as well. It is important to note that there is an inherent near-symmetry of SC-1 and SC-4 and this near-symmetry allows for direct access to (−)-b-Elemene-like compounds. In addition, both path A and B allows direct control over substituents at C4. For example, oxidation of the 2-propenyl group at C4 (this can be achieved directly on carvone) generates (−)-b-Elemene-6-one-like and (−)-b-Elemene-3-one-like derivatives that can be substituted at the C4 position readily (introducing group Q1). Indeed, removal of the 2-propenyl group at C4 can be achieved by oxidation of the olefin to the ketone followed by retro-Claisen condensation. Derivitization of this isopropenyl unit is also readily achieved. Thus, a wide range of Q1 and R3 groups can be introduced selectively at C4.

C5. Following standard protocols, a,a-disubstituted ketones, for example, a,a-dimethyl ketone and other compositions related to (−)-b-Elemene-6-one, can be selectively derivitized in the C5 position taking recourse to enolate chemistry and giving rise to U3 and V3 substituents. C6. Modifications at C6 can be achieved in a manner analogous to modifications at C3, i.e. carbonyl derivatives can readily be prepared stereoselectively and further modification, for example, olefination, as well as other substituents can be added including a wide range of E1 and V1 substituents.

In addition to the changes outlined, it should be noted that ring expansion and ring contraction can also be achieved to give rise to (−)-beta-Elemene derivatives containing either five or seven atoms in the central ring. The identity of W can be a carbon, nitrogen, or oxygen, and can also, in the case of carbon bearing substituents equivalent to U and V identity. Similarly, if W is nitrogen the group R can be widely varied to include a wide range of substituents as outlined below.

(−)-beta-elemene Analogs Synthesis and Composition Claims

The inventors claim the discovery of the unexpectedly efficacious, safe, non-toxic, and broadly applicable use of (−)-beta-elemenol, (−)-beta-elemenal, and (−)-beta-elemene fluoride, as anti-cancer chemotherapeutics. Moreover, the composition of (−)-beta-elemenol, (−)-beta-elemenal, (−)-beta-elemene fluoride and their analogs are claimed. The synthesis of (−)-beta-elemenol, (−)-beta-elemenal, (−)-beta-elemene fluoride is unambiguously established. (−)-beta-elemene fluoride is a novel compound, never synthesized previously. The uses of (−)-beta-elemenol, (−)-beta-elemenal, (−)-beta-elemene fluoride, and their analogs formulated singularly or in combination for anti-cancer applications are also claimed.

It is of interest to note that (−)-beta-elemenal has not been the subject of total chemical synthesis in either racemic or enantiomerically pure form. Enantiomeric purity is critical for proper evaluation of a drug. For example, Thalidimide enantiomers are either highly effective medicines or horribly disfiguring teratogens, depending on the enantiomer. Given the major impact that our recent clinical studies of (−)-betaelemene formulated alone and in conjugation suggest, the inventors claim the synthesis of (−)-beta-Elemenal and its analogs.

A mixture containing (−)-beta-elemenal and other herbal extracts has been purified from plants (Ito, S, Endo, K, Honma, H, and Ota, K, New constitutes of Thujopsis Dolabrata, Tetrahedron Letters, 1965, 42, 3777-3781. and de Kraker, J, et al. Germacrenes from fresh costus roots, Phytochemistry 2001, 58, 481-487). In a mixture, the single activity of (−)-beta-elemenal cannot be accessed. In our invention, we unambiguously derived (−)-beta-elemenal from pure (−)-beta-elemene (98% pure) and used NMR and rotation experiment to prove its structure.

A substance claimed to be beta-elemenal was identified in the bile of rats treated with 98% beta-elemene as a metabolite of beta-elemene. However, the metabolite data never rigorously established the relative or absolute stereochemistry of the substance. And its biological activity was never accessed. The inventors in this patent, for the first time, established biological activity of pure (−)-beta-elemenal, detailed below.

2) Anti-tumor Usage Claims

Derivatives of (−)-Beta-elemene Synthesized and Tested for Tumor Cell Line Growth Inhibition Ten derivatives of (−)-beta-elemene (FIG. 6), and three more (−)-beta-elemene analogs (FIG. 8) are synthesized and tested for in vitro tumor cell line inhibition.

In addition, the invention provides a method of treating cancer in a subject suffering therefrom comprising administering to the subject a therapeutically effective amount of any of the analogues related to (−)-beta-elemene disclosed herein optionally in combination with a pharmaceutically suitable carrier. The method may be applied where the cancer is a solid tumor or leukemia. In particular, the method is applicable where the cancer is brain tumor, lung cancer, breast cancer, prostate cancer, ovarian cancer, colorectal cancer, gastric intestinal cancer, or stomach cancer.

The subject invention also provides a pharmaceutical composition for treating cancer comprising any of the analogues of (−)-beta-elemene disclosed hereinabove, as an active ingredient, optionally though typically in combination with a pharmaceutically suitable carrier. The pharmaceutical compositions of the present invention may further comprise other therapeutically active ingredients.

The compounds above which are related to (−)-beta-elemene are useful in the treatment of cancer, and particularly, in cases where multidrug resistance is present, both in vivo and in vitro. The ability of these compounds as non-substrates of MDR in cells, as demonstrated in the Tables below, shows that the compounds are useful to treat, prevent or ameliorate cancer in subjects suffering therefrom.

The magnitude of the therapeutic dose of the compounds of the invention will vary with the nature and severity of the condition to be treated and with the particular compound and its route of administration. In general, the daily dose range for anticancer activity lies in the range of 3-300 mg/kg of body weight in a mammal, preferably 10-40 mg/kg, in single or multiple doses.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular, intraarterial, and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

The present invention will be better understood from the Experimental Details that follow. However, one skilled in the art will readily appreciate that the specific methods and results discussed are merely illustrative of the invention as described in the claims that follow thereafter. It will be understood that the processes of the present invention for preparing (−)-beta-elemenol, (−)-beta-elemenal, and (−)-beta-elemene fluoride, analogs thereof and intermediates thereto encompass the use of various alternate protecting groups known in the art. Those protecting groups used in the disclosure including the Examples below are merely illustrative.

3) Combination Therapy for Cancer Treatment (−)-beta-elemene, its derivatives, and its analogs are useful in the treatment of cancer, and in cases where multidrug resistance (MDR) is present, both in vivo and in vitro. The ability of these compounds as non-substrates of MDR in cells, as demonstrated in the Examples below, shows that the compounds are useful to treat, prevent or ameliorate cancer in subjects suffering therefrom MDR effect.

The preferred mode of invention without limiting its use or use of pharmaceutical equivalents to those described herein is to administer a therapeutic dose of a cisplatin, or 5-FU, or Taxol, or one of Taxol derivatives in combination with a therapeutic dose of the substance detailed above [one of (−)-beta-elemene, its derivatives, and its analogs] starting with the minimum recommended doses of each drug. (−)-betaelemene is shown to increase the efficacy of Cisplatin, or 5-FU, or Taxol, or one of Taxol derivatives in cancer cell line experiments. The substances detailed above are (−)-beta-elemene analogs, and thus they may possess the same ability.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A therapeutic change is a change in a measured biochemical characteristic in a direction expected to alleviate the disease or condition being addressed. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The term "therapeutic window" is intended to mean the range of dose between the minimal amount to achieve any therapeutic change, and the maximum amount, which results in a response that is the response immediately before toxicity to the patient.

The dosage regimen utilizing cisplatin taxol, paclitaxol, taxotere or 5FU in combination with the substance detailed above [one of (−)-beta-elemene, its derivatives, and its analogs] is selected in accordance with a variety of factors including type, species, age, weight, sex and medical condition of the patient; the severity of the condition to be treated; the route of administration; the cardiac, renal and hepatic function of the patient; and the particular compound or salt or ester thereof employed. Dosages in all events should be limited to the therapeutic window. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective amount.

Elemene kills cancer cells by induction of apoptosis and cell cycle arrest. Other anti-cancer agents stop uncontrolled cancer cell growth through different mechanisms, such as blockage of signaling transduction pathways, or acting as kinase inhibitors. Thus by combining Elemene with one or more of anti-cancer agents with different molecular mechanism could be an effective method for cancer treatment, similar to AIDS cocktail drug regime.

The subject invention provides a pharmaceutical composition for treating cancer comprising 1) one or more of the anti-cancer agents, including, but not limited to: cisplatin, taxol, taxol derivatives, 5FU, and other anti-cancer agent with different molecular mechanism from Elemene to combat cancer and 2) the substance detailed above [one or more of (−)-beta-elemene, its derivatives, and its analogs], optionally though typically in combination with a pharmaceutically suitable carrier. The pharmaceutical compositions of the present invention may further comprise other therapeutically active ingredients. The subject invention further provides a method of treating cancer in a subject suffering wherefrom comprising administering to the subject a therapeutically effective amount of 1) one or more of the anti-cancer agents, including, but not limited to: cisplatin, taxol, taxol derivatives, 5FU, and other anti-cancer agent with different molecular mechanism from Elemene to combat cancer, and 2) one or more of (−)-beta-elemene and its related and 3) a pharmaceutically suitable carrier. The method is especially useful where the cancer is a solid tumor, such as brain tumor, lung cancer, ovarian cancer, bladder cancer, cervical cancer, colon cancer, breast cancer, and prostate cancer.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc. The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

REFERENCES

Herout, V., Motl, O., Sorm, F., Coll. Czech. Chem. Commun 19, 990, 1954.

Xu, X. J. et al. Studies of β-Elemene's induction of human liver cancer cells, Chinese Journal of Clinical Oncology, Jul. 30-32, 1999.

Yuan. J et al. Elemene induces apoptosis and regulates expression of bcl-2 protein in human leukemia K562 cells, Zhongguo Yao Li Xue Bao (Chinese Pharmacology Journal), 20: 103-106, 1999.

Qian, J. et al. The studies of Elemene Emulsion on the Reversion of human lung cancer cells, Chinese Journal of Clinical Oncology, Jul. 7-10, 1999.

Qiang, J. et al. The induction of Differentiation of B16 cells y Elemene Emulsion, Chinese Journal of Clinical Oncology, Jul. 16-19, 1999.

Wang, B. C. et al. The Experimental Studies of Association between Elemene and Tumor Multidrug Resistance, Chinese Journal of Clinical Oncology, Jul. 10-13, 1999.

Qian, J., New anti-tumor drug, Elemene's pharmacology and Clinical results, Chinese Journal of Clinical Oncology, Jul. 1-3, 1999.

Wang, B. C. et al. The Experimental Studies of Association between Elemene and Tumor Multidrug Resistance, Chinese Journal of Clinical Oncology, Jul. 10-13, 1999.

Qian, J., New anti-tumor drug, Elemene's pharmacology and Clinical results, Chinese Journal of Clinical Oncology, Jul. 1-3, 1999.

Yang, X, and Page, M, P-glycoprotein expression in ovarian cancer cell line following treatment with cisplatin, Oncol. Res. 1995, 7(12): 619-24

Baekelandt, M., Covelli, A., Tropi, C., and Kristensen, S., Phase I/II trial of cisplatin and doxorubicin with SDZ PSC 833 in patients with refractory ovarian cancer, Proc. Annu. Meet. Am. Soc. Clin. Oncol 1997; 16: A757

Li, Z. et al. Studies on metabolite of beta-elemene in rat bile, Yao Xue Xue Bao. November 2000;35(11):829-31.

Ito, S, Endo, K, Honma, H, and Ota, K, New constitutes of Thujopsis Dolabrata, Tetrahedron Letters, 1965, 42, 3777-3781.

de Kraker, J, et al. Germacrenes from fresh costus roots, Phytochemistry 2001, 58, 481-487.

Wang, G. et al. Anti-tumor effect of P-elemene in non-small-cell lung cancer cells is mediated via induction of cell cycle arrest and apoptotic cell death, Cell. Mol. Life. Sci., 62 (2005), in press.

EXAMPLES

Example 1

Synthesis of ##STR3##

(E)-Geranyl 3-Methyl-3-butenate

A solution of geraniol (225 ul, 1.29 mmol, 1.0 equivalent) and triethylamine (271 ul, 1.94 mmol, 1.5 equivalent) in dry dichloromethane (I ml) was cooled to −78 C and treated dropwise with 3,3-dimethylacryloyl chloride (159 ul, 1.43 mmol, 1.1 equivalent). After 3 h, the solution was diluted with water (1 ml) and dichloromethane (1 ml), and the cooling bath was removed. The mixture was extracted with dichloromethane (3×20 ml), and the combined organics were dried (MgSO4) and concentrated in vacuo. Purification by radial chromatography (4 mm SiO2 plate; elute, 7% EatOAc-hexanes; product, fractions 4-6; 30 ml/fraction) afforded ##STR3## (301 mg, 1.27 mmol, 99% yield) as a clear oil: Rf starting material, 0.14; product, 0.51 (5:1 hexanes-EtOAc, anisaldehyde); FTIR (film) 2970, 2919, 2858, 1738, 1653, 1445, 1377, 1206, 1153, 987, 896 cm-1; sup. 1H NMR (400 MHz, CDCl3) δ 5.31-5.35 (m, 1H), 5.04-5.08 (m, 1H), 4.88 (bs, 1H), 4.83 (bs, 1H), 4.60 (s, 1H), 4.58 (s, 1H), 3.01 (s, 2H), 2.00-2.09 (m, 4H), 1.79 (s, 3H), 1.69 (s, 3H), 1.66 (s, 3H), 3.01 (s, 2H), 2.00-2.09 (m, 4H), 1.79 (s, 3H), 1.69 (s, 3H), 1.66 (s, 3H), 1.58 (s, 3H); .sup.13 C NMR (101 Mhz, CDCl3) δ 171.2, 142.2, 138.6, 131.7, 123.7, 118.2, 114.5, 61.4, 43.4, 39.4, 26.2, 25.6, 22.3, 17.6, 16.4; HRMS (EI, Pos) m/z calculated for [C15H24O2]+236.1776, found 236.1768.

Example 2

Synthesis of ##STR4a##

(2S,3S)-2-Isopropenyl-3,7-dimethyl-3-vinyl-6-octenoic Acid

The 3,5-bis(trifluoromethyl)benzenesulfonamide of (R,R)-1,2-diphenyl-1,2-diaminoethane (718 mg, 0.940 mmol, 1.0 equivalent) was dried under vacuum at 70 C for 3 h. The reaction flask was then evacuated and flushed three times with dry N2. Freshly distilled dichloromethane (32 ml) was added, and the homogeneous solution was cooled to −78 C. After 10 min, freshly distilled Bbr3 (3.76 ml, 0.5 M in CH2Cl2, 1.88 mmol, 2.0 equivalent) was added, and the solution was stirred for 5 min at −78 C and then warmed to 23 C. After 16 h, all volatile materials were removed under vacuum, the resulting white solid was redissolved in dichloromethane (20 ml), and the solution was concentrated again. After 60 min, the flask was evacuated and flushed three times with N2, and the resultant white solid was dissolved in freshly distilled toluene (32 ml). The bromoborane complex (##STR1##) was cooled to −78 C, Et3N (983 ul, 7.05 mmol, 7.5 equivalent) was added dropwise, and the mixture was stirred to effect solution (25 min). A precooled solution of ##STR3## (175 mg, 0.740 mmol, 0.8 equivalent) in toluene (4 ml) was added dropwise at −78 C, and the resultant solution was stirred at −70 C for 27 h and subsequently warmed to 4 C. After 36 h, the reaction solution was warmed to 23 C, diluted with diethyl ether (40 ml), acidified to pH 1 with 10% HCl, and extracted with diethyl ether (4×60 ml). The ethereal extract was dried (MgSO4) and concentrated in vacuo to give a 3:1 mixture of ##STR4a## and a minor diastereomer as a yellow oil (149.2 mg, 0.631 mmol, 85% yield): Rf starting material, 0.71; product, 0.26 (5% MeOH-CHCl3, Verghns); FTIR (film) 3084, 3055, 2972, 2927, 2859, 2729, 1707, 1638, 1452, 1413, 1377, 1265, 916, 742 cm-1; .sup.1H NMR (400 MHz, CDCl3) δ 6.09, 5.86 (dd, 1H, J=10.9, 17.5, major), 4.96-5.12 (m, 5H0, 3.08 (s, 1H, major), 3.07 (s, 1H, minor), 1.85-1.91 (m, 2H), 1.85 (s, 3H), 1.67 (s, 3H), 1.60 (s, 3H), 1.41-1.57 (m, 2H), 1.18 (s, 3H, major), 1.12 (s, 3H, minor); HRMS (EI, Pos) m/z calculated for [C15H24O2]+236.1776, found 236.1783.

Example 3

Synthesis of ##STR4b##

(2S,3S)-2-Isopropenyl-3,7-dimethyl-3-vinyl-6-octenol

A mixture of ##STR4a## and minor diastereomer (18 mg, 0.076 mmol, 1.0 equivalent) in dry diethyl ether (2 ml) was treated with LiAlH4 (15 mg, 0.381 mmol, 5.0 equivalent) at 23 C. After 12 h, additional LiAlH4 (15 mg, 0.381 mmol, 5.0 equivalent) and diethyl ether (2 ml) were added. After an additional 12 h, H2O (50 ul), NaOH (15% w/v, 50 ul), and H2O (150 ul) were added sequentially. The mixture was stirred for 10 min, filtered, dried (MgSO4), and concentrated in vacuo. Flash chromatography (10 g of SiO2; eluent, 10% EtOAc-hexanes; product, fractions 7-21; 10 ml/fraction) yielded a 3:1 mixture of ##STR4b## and minor diastereomer as a clear oil (15.8 mg, 0.071 mmol, 93% yield): Rf starting material, 0.46; product, 0.72 (12% MeOH-CHC13, anisaldehyde). The 3:1 mixture of diastereomers was separated by AgNO3-impregnated radial chromatography (4 mm SiO2 plate; eluent, 4:1 EtOAc-hexanes; minor, fractions 11-15; ##STR4b##, fractions 16-35; 30 ml/fraction) followed by passage through silica gel (20 g; 200 ml of 10% EtOAc-hexanes) to afford diastereomerically pure ##STR4b##: AgNO3-impregnated TLC: Rf ##STR4b##, 0.20; minor 0.35 (12% MeOH-CHC13. anisaldehyde). The enantiomeric purity of ##STR4b## was determined to be greater than 99:1 by chiral high-performance liquid chromathography (Chiralcel OD colume, 1% 2-propanol-hexanes, 214 nm, 1 ml/min, retention times S,S-isomer, ##STR4b##=9.4 min, R,R-isomer=23 min): $[\alpha]^{23}_D$−40.2° (c=0.54, CHCl3); FTIR (film) 3377, 3080, 2969, 2925, 2858, 1639, 1450, 1414, 1376, 1033, 1005, 912, 893 cm-1; .sup.1 H NMR (500 MHz, CDCl3) δ 5.80 (dd, 1H, J=10.8, 17.5), 5.02-5.08 (m, 3H), 4.91 (dd, 1H, J=1.3, 17.5), 4.83 (d, 1H, J=1.6), 3.72 (dd, 1H, J=4.3, 10.7), 1.82-1.90 (m, 2H), 1.77 (m, 3H), 1.67 (d, 3H, J=0.8), 1.57 (s, 3H), 1.30-1.44 (m, 2H), 1.04 (s, 3H); .sup.13 C NMR (101 MHz, CDCl3) d 144.4, 144.3, 131.3, 124.7, 115.7, 112.8, 61.1, 58.6, 41.2, 39.4, 25.7, 23.2, 22.6, 20.8, 17.6; HRMS (CI, NH3) m/z calculated for [C15H26O]+NH3 240.2327, found 240.2317.

Example 4

Synthesis of ##STR4c##

(2S,3S)-2-Isopropenyl-3,7-dimethyl-3-vinyl-6-octenal

A suspension of Dess-martin reagent (232 mg, 0.546 mmol, 1.5 equivalent) in dry dichloromethane (5 ml) was added to ##STR4b## (81 mg, 0.364 mmol, 1.0 equivalent) in dichloromethane (2 ml) at 23 C. After 1 h, the solution was filtered through Celite 545, concentrated in vacuo, rediluted in hexanes, and filtered through Celite 545. The filtrate was concentrated in vacuo and purified by flash chromatography (10 g of SiO2;eluent, 4% EtOAc-hexanes, product, fractions 4-8; 10 ml/fraction) to afford ##STR4c## (79 mg, 0.359 mmol, 98% yield) as a clear oil; Rf starting material, 0.28; product, 0.58 (5:1 hexanes-EtOAc, anisaldehyde); $[\alpha]^{23}_D$-40.2° (c=0.91, CHCl3); FTIR (film) 2970, 2921, 2859, 1721, 1638, 1453, 1377, 914 cm-1; .sup.1 H NMR (500 MHz, CDCl3) δ 9.65 (d, 1H, J=4.5), 5.92 (dd, 1H, J=10.9, 17.6), 5.14-5.17 (m, 2H), 5.06 (t, 1H, J=7.1), 5.00 (d, 1H, J=17.6), 4.88 (s, 1H), 2.70 (s, 3H), 1.38-1.50 (m, 2H), 1.15 (s, 3H), 1.67 (s, 3H), 1.57 (s, 3H), 1.38-1.50 (m, 2H), 1.15 (s, 3H); sup.13 C NMR (126 MHz, CDCl3) d 202.0, 143.1, 139.5, 131.5, 124.2, 116.8, 114.2, 67.1, 42.3, 39.1, 25.7, 25.6, 22.4, 20.6, 17.6; HRMS (EI, Pos) m/z calculated for [C15H24O]+ 220.1827, found 220.1817.

Example 5

Synthesis of ##STR5a##

(1S,2S,3 S,6S)-2,6-Diisopropenyl-3-methyl-3-vinyl-cyclohexanol

Diethylaluminum chloride (210 ul, 1.8 M in toluene, 0.379 mmol, 1.1 equivalent) was added dropwise to a solution of ##STR4c## (76 mg, 0.344 mmol, 1.0 equivalent) in dry dichloromethane (10 ml) at −78 C. Agter 1.5 h, triethylamine (500 ul) was added, the cooling bath was removed, and the solution was added to a mixture of saturated NaHCO3 (20 ml) and dichloromethane (2×20 ml), and the organic fractions were combined, dried (MgSO4), and concentrated in vacuo. Flash chromatography (15 g of SiO2; eluent, 4% EtOAc-hexanes; product, fractions 11-23; 10 ml/fraction) afforded a 96:4 mixture of ##STR5a## and a minor diastereomer (70.1 mg, 0.318 mmol, 92% yield): Rf starting material, 0.58; product, 0.41 (5:1 hexanes-EtOAc, anisaldehyde). The diastereomeric mixture was separated by AgNO3-impregnated radial chromatography (2 mm plate; eluent, 5:1 EtOAc-hexanes; product, fractions 10-33; 3 ml/fraction) followed by passage through silica gel (10 g; 150 ml of 4% EtOAc-hexanes) to afford pure ##STR5a## (88% yield) as a clear oil: AgNO3-impregnated TLC: Rf ##STR5a##, 0.08; minor, 0.17 (12% MeOH—CHCl3; anisaldehyde); $[\alpha]_D$+17.8° (c=0.91, CHCl3); FTIR (film) 3566, 3486, 2969, 2931, 1639, 1454, 1375, 1004, 910, 889 cm-1; sup.1 H NMR (500 MHz, CDCl3) δ 5.78 (dd, 1H, J=10.9, 17.4), 5.06 (s, 1H), 4.88-4.92 (m, 4H), 4.76 (s, 1H), 3.77 (t, 1H, J=10.4), 2.08 (dt, 1H, J=4.8, 10.8), 1.98 (d, 1H, J=10.4), 1.90 (bs, 1H), 1.80 (s, 3H), 1.79 (s, 3H), 1.51-1.66 (m, 3H), 1.42 (dt, 1H, J=3.1, 13.0), 1.06 (s, 3H); sup.13 C NMR (101 MHz, CDCl3) d 148.9, 147.1, 144.2, 114.1, 112.2, 110.3, 69.3, 59.7, 53.7, 41.3, 39.0, 26.2, 25.0, 19.5, 18.1; HRMS (EI, Pos) m/z calculated for [C15H24O]+220.1827, found 220.1826.

Example 6

Synthesis of ##STR5b##

Reaction of 2-chloro-1,3-dimethyl-1,3,2-diazaphospholane with ##STR5a## to get ##STR5b##

2-chloro-1,3-dimethyl-1,3,2-diazaphospholane (10 ul, 0.076 mmol, 1.4 equivalent) was added dropwise to a solution of ##STR5a## (12 mg, 0.054 mmol, 1.0 equivalent) and triethylamine (8 ul, 0.06 mmol, 1.1 equivalent) in dry dichloromethane (1 ml) at 23 C. After 75 min, hydrogen peroxide (7 ul, 30% aqueous solution, 0.065 mmol, 1.2 equivalent) was added, and the reaction was stirred vigorously for 10 min and then quenched with sat Na2SO4 (1 ml). After 5 min of vigorous stirring, the solution was added to a mixture of dichloromethane (20 ml) and water (20 ml). The aqueous portion was extracted with dichloromethane (2×20 ml), and the combined organic fractions were dried (Na2SO4) and concentrated in vacuo. Flash chromatography (10 g SiO2; eluent 1% MeOH—CHCl3; product, fractions 12-15; 10 ml/fraction) afforded in addition to recovered ##STR5a## (2.5 mg, 21% yield), ##STR5b## (15 mg, 0.042 mm01, 77% yield, 92% after two cycles) as a clear oil: Rf starting material, 0.78; product, 0.35 (5% MeOH—CHCl3, Verghns); $[\alpha]^{23}_D$+25.4° (c=1.03, CHCl3); FTIR (film) 3079, 2934, 2880, 1647, 1451, 1269, 1240, 1161, 1003, 941 cm-1; sup.1 H NMR(500 MHz, CDCl3)δ 5.74 (dd, 1H, J=10.3), 2.93-3.04 (m, 4H), 2.50-2.54 (m, 6H), 2.17-2.22 (m, 1H), 2.00-2.06 (m, 1H), 1.87 (s, 3H), 1.36-1.70 (m, 4H), 1.04 (s, 3H); sup.13 C NMR (101 MHz, CdCl3) δ 148.5, 146.9, 142.7, 114.6 (bm), 112.9, 110.4, 77.8 (bm), 58.7 (bm), 53.8, 47.3 (d), 41.7, 38.7, 33.8, 33.6, 27.9, 20.3, 18.3; sup.31 P NMR (121 MHz, CDCl3, Ph3P external standard at −6 ppm) δ 22.65 (t, J=10); HRMS (EI, Pos) m/z calculated for [C19H33O2N2P]+352.2280, found 352.2285.

Example 7

Synthesis of ##STR6##
(−)-Beta-elemene

A solution of dry ##STR5b## (53 mg, 0.152 mmol, 1.0 equivalent, azeotroped from toluene) and tert-amyl alcohol (67 ul, 0.608 mmol, 4.0 equivalent) in dry tetrahydrofuran (1.5 ml) was cannulated into a blue solution of excess lithium in liquid ammonia (5 ml) at −33 C. The transfer flask was rinsed with tetrahydrofuran (0.5 ml), and the solution was stirred for 10 h. The solution was sequentially quenched dropwise with isoprene (ca. 300 ul) and saturated aqueous NH4Cl (2 ml) and diluted with pentanes (4 ml). After warming to 23 C, the solution was added to a mixture of pentanes (2×30 ml), and the combined organic fractions were dried (Na2SO4) and concentrated in vacuo. Flash chromatography (10 g SiO2; eluent, pentanes; product, fractions 4-7; 10 ml/fraction) afforded ##STR6## (29.5 mg, 0.144 mmol, 95% yield) as a clear oil: Rf starting material, 0.00; product, 0.71 (petanes, Verghns); $[\alpha]^{23}_D$−15.4° (c=0.59, CHCl3); FTIR (film) 3083, 2969, 2931, 1644, 1454, 1440, 1374, 1004, 909 cm-1; sup.1 H NMR (500 MHz, CDCl3) δ 5.82 (dd, 1H, J=11.0, 17.4), 4.88-4.92 (m, 2H), 4.82 (t, 1H, J=1.6), 4.70-4.72 (m, 2H), 4.59 (bs, 1H), 1.99-2.03 (m, 1H), 1.92-1.96 (m, 1H), 1.75 (s, 1H), 1.71 (s, 3H), 1.42-1.63 (m, 6H), 1.01 (s, 3H); sup.13 C NMR (101 MHz, CDCl3) δ 150.4, 150.3, 147.7, 112.1, 109.8, 108.2, 52.8, 45.7, 39.9, 39.8, 32.9, 26.8, 24.7, 21.1, 16.6; LRMS (EI, Pos) m/z calculated for [C15H24]+204.1878, found 204.1869.

Example 8

Synthesis of ##STR7##

(1S, 3R, 4R)-1-Acetyl-3-isopropenyl-4-methyl-4-vinylcyclohexane

A solution of (DHQD)2-PHAL (11 mg, 0.0137 mmol, 0.1 equivalent), potassium osmate (VI) dihydrate (0.5 mg, 0.0014 mmol, 0.01 equivalent), potassium ferrocyanide (135 mg, 0.411 mmol, 3.0 equivalent), potassium carbonate (57 mg, 0.411 mmol, 3.0 equivalent), and methanesulfonamide (13 mg, 0.137 mmol, 1.0 equivalent) in 1:1 2-methyl-2-propanol-water (1.5 ml) was cooled to 0 C. The biphasic mixture was added to ##STR6## (28 mg, 0.137 mmol, 1.0 equivalent) at 0 C and the reaction mixture was stirred for 11 h. The solution was quenched with excess Na2SO3 (until precipitate and color disappeared). After warming to 23 C, the solution was added to a mixture of dichloromethane (20 ml) and water (20 ml). The aqueous portion was extracted with dichloromethane (2×20ml), and the combined organic fractions were dried (Na2SO4) and concentrated in vacuo. Flash chromatography (15 g of SiO2; eluent, 28% EtOAc-hexanes; product, fractions 19-30; 10 ml/fraction) afforded, in addition to recovered ##STR6## (5 mg, 0.024 mmol, 17% yield), a 3:1 mixture of diastereomers of the 1,2-diol (24.8 mg, 0.104 mmol, 76% yield) as a clear oil.

Sodium periodate (62 mg, 0.289 mmol, 3.0 equivalent) was added to a solution of the 1,2-diol (23 mg, 0.096 mmol, 1.0 equivalent) in 4:1 tetrahydrofuran-water (2 ml) at 23 C. After 30 min, the solution was added to a mixture of dichloromethane (20 ml) and water (20 ml). The aqueous portion was extracted with dichloromethane (2×20ml), and the combined organic fractions were dried (Na2SO4) and concentrated in vacuo. Flash chromatography (10 g of SiO2; eluent, 7% EtOAc-hexanes; product, fractions 3-9; 10 ml/fraction) afforded ##STR7## (19 mg, 0.092 mmol, 96% yield) as a clear oil: Rf starting material, 0.07; product, 0.61 (3:1 hexanes-EtOAc, Verghns); $[\alpha]^{23}_D$+37.0° (c=1.0, CHCl3); FTIR (film) 3082, 2971, 2935, 2864, 1711, 1638, 1441, 1373, 1353, 908, 892 cm-1; sup.1 H NMR (500 MHz, CDCl3) δ 5.80 (dd, 1H, J=10.6, 17.8), 4.89-4.93 (m, 2H), 4.84 (t, 1H, J=1.4), 4.60 (s, 1H), 2.37-2.43 (m, 1H), 2.16 (s, 3H), 1.97-2.00 (m, 1H), 1.74-1.78 (m, 1H), 1.67-1.71 (m, 5H), 1.46-1.59 (m, 3J), 1.00 (s, 3H); sup.13 C NMR (101 MHz, CDCll3) δ 211.6, 149.6, 146.9, 112.6, 110.3, 52.0, 51.9, 39.6, 39.1, 29.4, 28.2, 24.7, 23.7, 16.5; HRMS (EI, Pos) m/z calculate for [C14H22O]+ 206.1671, found 206.1661.

Example 9

Synthesis of ##STR2##
(+)-Fuscol n-Butyllithium (244 ul, 1.57 M in hexanes, 0.384 mmol, 4.95 equivalengt) was added to a solution of 2-methyl-2-propanol (37 ul, 0.388 mmol, 5.0 equivalent) in tetrahydrofuran (0.5 ml) at −78 C. After 15 min, butyl (dibutylphosphono)-2-butenoate (108 ul, 0.388 mmol, 5.0 equivalent) was added, and the mixture was briefly warmed to effect solution. After 15 min at −78 C, the yellow phosphonate anoin solution was cannulated into ##STR7## (16 mg, 0.078 mmol, 1.0 equivalent) in tetrahydrofuran (0.5 ml) at 23 C. After 18 h, 5 equivalent of additional phosphonate anion was added in the same manner. This process was repeated at 28 and 41 h. After 48 h of stirring, the reaction mixture was diluted in dichloromethane, passed through silica gel (15 g, 200 ml CH2Cl2), and concentrated in vacuo. Flash chromatography (15 g of SiO2; eluent, 1.5% EtOAc-hexanes; product, fractions 7-15; 10 ml/fraction) afforded butyl 5-[(1'S,3'R,4'R)-3'-isopropenyl-4'-methyl-4'-vinylcyclohexyl]-(E,E)-hexadienoate (22.1 mg, 0.067 mmol, 87% yield) as a 12:1 mixture of diastereomers: Rf starting material, 0.55; product, 0.75 (5:1 hexanes-EtOAc, anisaldehyde). Preparative thin layer chromatography (0.5 mm plate, 9:1 pentanes-diethyl ether, Rf trans, trans-5-[(1'S,3'R,4'R)-3'-isopropenyl-4'-methyl-4'-vinylcyclohexyl]-(E,E)-hexadienoate, 0.42) afforded pure 5-[(1'S,3'R,4'R)-3'-isopropenyl-4'-methyl-4'-vinylcyclohexyl]-(E,E)-hexadienoate (80% yield) as a clear oil: $[\alpha]^{23}_D$+24.5° (c=1.17, CHCl3).

Methyllithium (161 ul, 1.5 M in diethyl ether, 0.242 mmol, 5.0 equivalent) was added to a solution of 5-[(1'S,3'R,4'R)-3'-isopropenyl-4'-methyl-4'-vinylcyclohexyl]-(E,E)-hexadienoate (16 mg, 0.048 mmol, 1.0 equivalent) in diethyl ether (2 ml) at −30 C. After 12 h, the reaction was quenched with aqueous NH4Cl, warmed to 23 C, and added to a mixture of diethyl ether (10 ml) and water (10 ml). The aqueous portion was extracted with diethyl ether (2×20 ml), and the combined organic fractions were dried (Na2SO4) and concentrated in vacuo. Flash chromatography (15 g of SiO2; eluent,-6% EtOAc-1% triethylamine-hexanes; product, fractions 10-20; 10 ml/fraction) afforded ##STR2## (12.5 mg, 0.043 mmol, 90% yield) as a clear oil: Rf starting material, 0.75; product, 0.27 (5:1 hexanes-EtoAc, anisaldehyde); $[\alpha]^{23}_D$+19.7° (c=1.0, CHCl3); FTIR (film) 3402, 3360, 3082, 2971, 2928, 2860, 1637, 1441, 1374, 966, 908, 890 cm-1; UV/vis λmax=240 nm, ϵ=35,000; sup.1 H NMR (500 MHz, CDCl3) δ 6.48 (dd, 1H, J=10.8, 15.3), 5.87 (d, 1H, J=10.8), 5.82 (dd, 1H, J=11.1, 17.2), 5.76 (d, 1H, J=15.3), 4.88-4.92 (m, 2H), 4.81 (t, 1H), J=1.5), 4.58 (s, 1H), 2.01 (dd, 1H, J=3.5, 12.6), 1.95-1.98 (m, 1H), 1.79 (s, 3H), 1.70 (s, 3H), 1.43-1.60 (m, 6H), 1.35 (s, 6H), 1.00 (s, 3H); sup.13 C NMR (126 MHz, CDCl3), δ 150.2, 147.6, 143.4, 139.3, 123.1, 122.3, 112.1, 109.9, 70.9, 52.8, 47.7, 39.9, 39.8, 32.7, 29.9, 26.6, 24.7, 16.7, 15.3; HRMS (EI, Pos) m/z calculated for [C20H32O]+288.2453, found 288.2440.

Example 10

Synthesis of ##STR9## (Lr-1)

(R)-2-((1R,3S,4S)-3-isopropenyl-4-methyl-4-vinylcyclohexyl)-propane-1,2-diol $^1$H NMR (400 Mhz, CDCl3): δ=6.10 (1H, dd, J=17.6, 10.8 Hz), 5.15 (1H, d, J=18 Hz) 5.06 (1H, d, J=10.8 Hz), 4.70 (2H, s), 3.42 (1H, dd, J=11.2, 8.4 Hz), 3.23 (1H, dd, J=11.2, 5.2 Hz), 2.78 (1H, s), 2.15 (1H, dd, J=8.0, 5.2 Hz), 2.01 (1H, dd, J=12.4, 3.2 Hz), 1.93 (1H, tt, J=12.0, 3.2 Hz), 1.73 (3H, s), 1.61-1.56 (1H, m), 1.52-1.24 (5H, series of m), 1.26 (3H, s), 1.09 (3H, s).

Example 11

Synthesis of ##STR10## (Lr-2)

(S)-2-((1R,3S,4S)-3-isopropenyl-4-methyl-4-vinylcyclohexyl)-propane-1,2-diol $^1$H NMR (400 Mhz, CDCl3): δ=5.79 (1H, dd, J=17.6, 10.8 Hz), 4.81-4.91 (3H, m), 4.58 (s, 0.5 H), 4.56 (s, 0.5 H), 3.58 (1H, 1/2ABq, J=10.8 Hz), 3.43 (1H, 1/2ABq, J=10.8 Hz), 2.26 (1H, br s), 2.08 (1H, br s), 1.96 (1H, dd, J=12.4, 4.0 Hz), 1.70 (s, 1.5 H) and 1.69 (s, 1.5 H), 1.64-1.22 (7H, series of m), 1.14 (3H, s), 0.98 (3H, s).

Example 12

Synthesis of ##STR11## (Lr-3)

1-((1R,3S,4S)-3-Isopropenyl-4-methyl-4-vinyl-cyclohexyl)-ethanone $^1$H NMR (400 Mhz, CDCl3): δ=5.89 (1H, dd, J=17.6, 10.4 Hz), 4.91 (1H, d, J=13.6 Hz), 4.91 (1H, d, J=15.6 Hz), 4.84

(1H, s), 4.60 (1H, s), 2.46-2.36 (1H, s), 2.16 (3H, s), 1.99 (1H, dd, J=9.2, 7.2 Hz), 1.79-1.66 (2H, m), 1.71 (3H, s), 1.57-1.44 (4H, m), 0.99 (3H, s),

Example 13

Synthesis of ##STR12## (Lr-4)

(S)-1,5-Diisopropenyl-2-methyl-cyclohex-2-enol, and (R)-1,5-Diisopropenyl-2-methyl-cyclohex-2-enol $^1$H NMR (400 Mhz, CDCl3): δ=1.55 (t, 1H, 2JHH=12.5 Hz), 1.61 (br s, 1H), 1.67 (s, 3H), 1.72 (s, 3H), 1.81 (s, 3H), 1.94 (m, 0.5H), 1.97 (m, 0.5H), 2.03 (m, 0.5H), 1.97 (m, 0.5H), 4.72 0.5H), 2.10 (m, 0.5H), 2.15 (m, 0.5H), 2.25 (m, 1H), 1.94 (m, 0.5H), 1.97 (m, 0.5H), 4.72 (s, 2H), 4.81 (s, 1H), 4.97 (s, 1H), 5.62 (s, 1H)

Example 14

Synthesis of ##STR13## (Lr-5)

(S)-5-Isopropenyl-1,2-dimethyl-cyclohex-2-enol, and (R)-5-Isopropenyl-1,2-dimethyl-cyclohex-2-enol $^1$H NMR (400 Mhz, CDCl3): δ=1.33 (s,3H), 1.50 (bs, 1H), 1.66 (t, 1H, 2JHH=12.1 Hz), 1.74 (s, 6H), 1.89-1.98 (m, 2H), 2.09 (m, 1H), 2.30 (br t, 1H), 4.74 (s, 2H), 5.41 (s, 1H)

Example 15

Synthesis of ##STR14## (Lr-6)

(S)-3,5-Diisopropenyl-2-methyl-cyclohex-2-enone $^1$H NMR (400 Mhz, CDCl3): δ=1.75 (br s, 6H), 1.88 (s, 3H), 2.29-2.70 (m, 5H), 4.76 (s, 2H), 4.81 (s, 1H), 5.05 (s, 1H)

Example 16

Synthesis of ##STR15## (Lr-7)

(1S,5S)-3,5-Diisopropenyl-2-methyl-cyclohex-2-enol, and (1R,5S)-3,5-Diisopropenyl-2-methyl-cyclohex-2-enol $^1$H NMR (400 Mhz, CDCl3): δ=1.53 (t, 1H, xJHH=12.0 Hz), 1.65 (br s, 1H), 1.72 (s, 3H), 1.74 (s, 3H), 1.78 (s, 3H), 2.09-2.18 (m, 3H), 2.26 (br t, 1H), 4.18 (br t, 1H), 4.65 (s, 1 H), 4.73 (s, 1 H), 4.93 (s, 1 H)

Example 17

Synthesis of ##STR16## (Lr-8)

(1R,5S)-1-Isobutyl-3,5-diisopropenyl-2-methyl-cyclohex-2-enol, and (1S,5S)-1-Isobutyl-3,5-diisopropenyl-2-methyl-cyclohex-2-enol $^1$H NMR (300 Mhz, CDCl3): δ=0.92 (2, d, 3H), 0.99 (2,d, 3H), 1.54 (m, 2H) 1.72 (s, 3H), 1.74 (s, 3H), 1.83 (m, 1H), 1.87 (m, 1H), 1.95 (m, 1H), 2.10-2.18 (2 sets of m, 1H) 2.28 (br t, 1H), 4.74 (s, 2H), 5.37 (m, 1H)

Example 18

Synthesis of ##STR17## (Lr-9 and Lr-10)

(S)-5-Isopropenyl-2-methyl-cyclohex-2-enone, and (R)-5-Isopropenyl-2-methyl-cyclohex-2-enone $^1$H NMR (300 Mhz, CDCl3): δ=1.67 (s, 3H), 1.69 (s, 3H), 2.30-2.69 (m, 5H) 4.76 (s, 1H), 4.80 (s, 1H), 6.77 (br s, 1H)

Example 19

Synthesis of ##STR21##

(−)-Beta-elemenol

To a solution of (−)-beta-elemene (##STR6##, 98% pure, 780 mg, 3.823 mmol) in dichloromethane (DCM, 50 ml) was added $K_2CO_3$ (580 mg, 4.205 mmol) and cooled to 0° C. m-CPBA (70%/wt pure, 942 mg, 3.823 mmol) was added portion wise over a period of 15 minutes. After stirring for 2 h at 0° C., the white precipitate was removed by filtration and the precipitate was washed with DCM (10 ml). The combined organic phase was concentrated under reduced pressure at room temperature to afford a viscous clear liquid, which was further purified by (FCC, $SiO_2$). Elution with 3% ethyl acetate in hexanes gave unreacted (−)-beta-elemene (198 mg, 25%). Continued elution with 5% ethyl acetate in hexanes gave a 2:1 mixture of diastereomeric epoxides (450 mg, 53%), which was used as such for the next step without further purification. To a solution of diisopropylamine in dry ether (10 ml), cooled to −70° C. was added n-BuLi (5.96 ml of 1.6M solution in hexanes) and allowed to attain room temperature over 10 minutes. To this a solution of above epoxides (350 mg, 1.591 mmol) in dry ether (20 ml) was added dropwise and stirred under argon for 5 h at room temperature. The reaction was quenched with water (5 ml) and extracted with pentane (150 ml). The organic phase was washed with water (30 ml), brine (30 ml) and dried over $NaSO_4$. Evaporation of solvent gave a yellow viscous liquid, which upon purification (FCC, $SiO_2$) using 20% ethyl acetate in hexanes gave a 2:1 mixture of allylic alcohols (270 mg, 77%). The desired major isomer (##STR21##, (−)-beta-elemenol) was obtained in pure form by repeated column chromatography. Spectral data for ##STR21##, (−)-beta-elemenol: IR $v_{max}$ (neat)/cm$^{-1}$ 3336, 3080, 2928, 1639, 1439, 890; $δ_H$ (300 MHz, CDCl$_3$) 5.82 (1H, dd, J=15.0, 10.5) 5.05 (1H, bs), 4.95-4.92 (2H, m), 4.88 (1H, bs), 4.83 (bs, 1H), 4.59 (bs, 1H), 4.15 (bs, 2H), 2.10-1.98 (2H, m), 1.71 (3H, s), 1.70-1.40 (6H, series of m), 1.02 (3H, s); $δ_C$(75 MHz, CDCl$_3$) 153.8, 150.2, 147.6, 112.3, 110.1, 108.1, 65.5, 53.0, 41.7, 40.2, 40.1, 33.6, 27.5, 25.1, 16.9. $[α]_D^{25}$ −25 (c 0.9, CHCl$_3$).

Example 20

Synthesis of ##STR22##

(−)-Beta-elemenal

To $MnO_2$ (430 mg, activated at 150° C. under vacuum for 12 h) was added a solution of ##STR21##, (−)-beta-elemenol (43 mg, 0.195 mmol) in hexanes (5 ml) and stirred at room temperature for 25 min. $MnO_2$ was removed by filtration and the precipitate was washed with hexanes (5 ml). The filtrate was evaporated and the residue was purified (FCC, $SiO_2$) using 1:3 ethyl acetate-hexanes as eluent to give pure aldehyde ##STR22##, (−)-beta-elemenal as a clear liquid (34 mg, 80%). IR $v_{max}$ (neat)/cm$^{-1}$ 3081, 2927, 2698, 1691, 1637, 1438, 1372, 890; $δ_H$($^{300}$ MHz, CDCl$_3$) 9.53 (1H, s), 6.29 (1H, s), 5.99 (1H, s), 5.83 (1H, dd, J=17.7, 10.5), 4.94-4.82 (3H, series of m), 4.57 (bs, 1H), 2.62-2.48 (1H, m), 2.14-2.04 (1H, m), 1.71 (3H, s), 1.78-1.40 (6H, series of m), 1.03 (3H, s); $\delta_C$(75 MHz, CDCl$_3$) 194.6, 154.9, 150.0, 147.4, 133.1, 112.3, 110.2, 52.7, 40.0, 39.9, 36.7, 33.0, 27.1, 25.2, 16.9. $[\alpha]_D^{25}$ −35.4 (c 0.9, CHCl$_3$).

Example 21

Synthesis of ##STR23##

(−)-Beta-elemene Fluoride

To a solution of ##STR21##, (−)-beta-elemenol (38 mg, 0.173 mmol) in dry DCM (0.3 ml) cooled to −70° C. was added DAST (diethylaminosulfer trifluoride, 23 μl, 0.173 mmol) drop-wise and stirred under argon for 1.5 h during which the temperature was allowed to attain room temperature. The reaction mixture was quenched with saturated NaHCO$_3$ solution (1 ml) at 0° C. and extracted with DCM (15 ml). The organic phase was washed with water (6 ml×2), brine (10 ml) and dried. Evaporation of solvent gave a yellow residue, which was further purified (FCC, SiO$_2$) using 0.05% ethyl acetate in pentane as eluent to give an highly volatile, pure fluoride ##STR23##, (−)-beta-elemene fluoride, as a clear liquid (14 mg, 36%). IR $v_{max}$ (neat)/cm$^{-1}$ 3081, 2929, 1638, 1439, 1373, 995, 906; $\delta_H$(300 MHz, CDCl$_3$) 5.82 (1H, dd, J=17.7, 10.5), 5.11 (1H, d, J=2.7), 5.05 (1H, bs), 4.93 (2H, d, J=3.6), 4.89 (1H, bs), 4.84 (1H, t, J=1.2), 4.78 (1H, s), 4.60 (1H, bs) 2.18-2.00 (2H, m), 1.72 (3H, s), 1.71-1.44 (6H, series of m), 1.02 (3H, s); $\delta_C$(75 MHz, CDCl$_3$) 150.1, 147.5, 112.4, 111.9, 111.8, 110.2, 85.2 (d, J=664 Hz), 52.9, 41.1, 40.1, 40.0, 33.3, 27.3, 25.1, 16.9. $[\alpha]_D^{25}$ −61 (c 0.9, CHCl$_3$).

Example 22

In vitro Effect of Pure (−)-Beta-elemene's Inhibition of Cancer Cell Growth

The effect of pure (−)-beta-Elemene on antitumor activity in human carcinoma cells was determined by the MTT survival assay, or using a commercial MTT assay kit (Cell Titer 96 Aqueous One Solution Cell Proliferation Assay; Promega Corporation, Madison, Wis.) according to the manufacturer's instructions. The MTT assay is a commonly used method in evaluation of cell survival, based on the ability of viable cells to convert MTT, a soluble tetrazolium salt [3-(4,5-dimethylthuazole-2-yl)-2,5 diphenyl tetrazolium bromide], into an insoluble formazan precipitate, which is quantitated by spectrophotometry following solubilization in dimethyl sulfoxide (DMSO).

In brief, carcinoma cells treated with (−)-beta-Elemene alone, in 96-well tissue culture dishes were incubated with MTT (2 μg/ml) for 4 h. The cells were then solubilized in 125 μl of DMSO and absorbance readings were taken using a 96-well Opsys MRI Microplate Reader (ThermoLabsystems; Chantilly, Va.). The amount of MTT dye reduction was calculated based on the difference between absorbance at 570 nm and at 630 nm. Cell viability in treated cells was expressed as the amount of dye reduction relative to that of untreated control cells. The wells which contained only medium and 10 μl of MTT were used as blanks for the plate reader. Three sets of experiments were performed in 8-12 wells for each treatment.

TABLE 1

Effect of (−)-beta-Elemene on in vitro cytotoxicity in human cancer cells as assessed by the MTT assay

| Cancer cell type | Elemene IC$_{50}$ (·g/ml) | Elemene IC$_{50}$ (·M) |
| --- | --- | --- |
| A-172 brain tumor | 65 | 32 |
| U-87 brain tumor | 88 | 43 |
| STTG1 brain tumor | 82 | 40 |
| NCI-H596 lung cancer | 95 | 47 |
| H-460 lung cancer | 32 | 16 |
| H-69 lung cancer | 52 | 25 |
| A2780/CP70 ovarian cancer | 53 | 26 |
| MCAS ovarian cancer | 60 | 29 |
| SKOV-3 ovarian cancer | 67 | 33 |
| ES-2 ovarian cancer | 54 | 26 |
| 5637 bladder cancer | 82 | 40 |
| T-24 bladder cancer | 65 | 32 |
| CCL-2 (Hela) cervical cancer | 63 | 31 |
| HTB-33 cervical cancer | 68 | 33 |
| CCL-222 colon cancer | 47 | 23 |
| CCL-225 colon cancer | 67 | 33 |
| MCF-7 breast cancer | 93 | 46 |
| T47D breast cancer | 63 | 31 |
| DU-145 prostate cancer | 58 | 28 |
| PC-3 prostate cancer | 100 | 49 |

Example 23

In vivo Effect of Pure (−)-Beta-elemene's Inhibition of Tumor Growth
Efficacy Studies According to pharmacology studies, intravenous injection of (−)-beta-Elemene at 7.5, 15, 30, or 60 mg/kg, once per day for 10 days, can extend the life span of 1) nude mice xenographed in brain with human glioma cell line SHG-44 to 132.84, 140.46, 150.37, and 159.81% compared to control; and 2) nude mice xenographed in brain with mice glioma cell line G422 to 138.78, 144.90, 153.06, and 163.27% compared to control. These experiments were repeated and the results were consistent. The tumor inhibition rate on G422 glioma xenograph models (xenograph under skin) (3 concentrations) was 60.89%, 47.11%, and 32.00%, respectively. The tumor inhibition rate on SHG-44 glioma xenograph models (xenograph under skin) (3 concentrations) was 63.24%, 51.35%, and 37.83%, respectively.

TABLE 2

Efficacy of (−)-beta-Elemene, human glioma G422 (xenograph in brain)

| Sample | Dose mg/kg/time | Protocol | Animal No. (No.) Beginning/End | Starting Weight (g) | Average Life Span (day) $\overline{X} \pm SD$ | Life Extension Rate % |
| --- | --- | --- | --- | --- | --- | --- |
| β-Elemene | 60 | iv × 10 qd | 10/0 | 19.5 | 14.9 ± 2.1*** | 162.84 |
| β-Elemene | 30 | iv × 10 qd | 10/0 | 19.7 | 14.1 ± 2.3*** | 154.10 |
| β-Elemene | 15 | iv × 10 qd | 10/0 | 19.5 | 13.1 ± 2.7*** | 143.17 |
| β-Elemene | 7.5 | iv × 10 qd | 10/0 | 19.6 | 12.3 ± 3.4*** | 134.97 |

TABLE 2-continued

Efficacy of (−)-beta-Elemene, human glioma G422
(xenograph in brain)

| Sample | Dose mg/kg/time | Protocol | Animal No. (No.) Beginning/End | Starting Weight (g) | Average Life Span (day) $\overline{X} \pm SD$ | Life Extension Rate % |
|---|---|---|---|---|---|---|
| VM26 | 5 | ip × 7 qd | 10/0? | 19.7 | 21.5 ± 3.4*** | 234.97 |
| Neg. Cont. | Solvent | iv × 10 qd | 20/0 | 19.6 | 9.15 ± 1.6 | |

***$P < 0.01$, compared with negative control group, same in Table below.

According to anti-cancer drug pharmacology guideline, life extension rate for an anti-cancer drug has to be over 125% to be effective.

TABLE 3

Efficacy of (−)-beta-Elemene, human glioma SHG44
(xenograph in brain)

| Sample | Dose mg/kg/time | Protocol | Animal No. (No.) Beginning/End | Starting Weight (g) | Average Life Span (day) $\overline{X} \pm SD$ | Life Extension Rate % |
|---|---|---|---|---|---|---|
| β-Elemene | 60 | iv × 10 qd | 6/0 | 18.4 | 25.2 ± 3.1*** | 160.36 |
| β-Elemene | 30 | iv × 10 qd | 6/0 | 18.1 | 23.3 ± 3.6*** | 148.69 |
| β-Elemene | 15 | iv × 10 qd | 6/0 | 18.1 | 21.8 ± 1.9*** | 139.31 |
| β-Elemene | 7.5 | iv × 10 qd | 6/0 | 18.6 | 20.2 ± 1.7*** | 128.72 |
| VM26 | 5 | ip × 7 qd | 6/0 | 18.3 | 30.8 ± 3.7*** | 196.75 |
| Neg. Cont. | Solvent | iv × 10 qd | 12/0 | 18.5 | 15.7 ± 1.6 | |

***$P < 0.01$, compared with negative control group, same in Table below.

According to anti-cancer drug pharmacology guideline, life extension rate for an anti-cancer drug has to be over 125% to be effective.

TABLE 4

Efficacy of (−)-beta-Elemene (injection directly into tumor),
human glioma G-422 (xenograph under skin)

| Sample | Dose mg/kg | Protocol | Animal No. Beginning/End | Animal Weight Beginning/End | Tumor Weight X ± SD | Inhibition Rate % |
|---|---|---|---|---|---|---|
| β-Elemene | 60 | it × 10 qd | 10/10 | 20.2 24.4 | 0.88 ± 0.24*** | 60.89 |
| β-Elemene | 30 | it × 10 qd | 10/9 | 20.4 24.4 | 1.19 ± 0.55*** | 47.11 |
| β-Elemene | 15 | it × 10 qd | 10/10 | 20.6 25.1 | 1.53 ± 0.27*** | 32.00 |
| Pos. Cont. VM-26 | 5 mg | ip × 10 qd | 10/10 | 20.2 22.4 | 0.32 ± 0.12*** | 85.78 |
| Neg. Cont. | Solvent | it × 10 qd | 20/19 | 20.5 25.7 | 2.25 ± 0.36 | |

*** $P < 0.01$, compared with negative control group.

TABLE 5

Efficacy of (−)-beta-Elemene (injection directly into tumor),
human glioma SHG-44G (xenograph under skin)

| Sample | Dose mg/kg | Protocol | Animal No. Beginning/End | Animal Weight Beginning/End | Tumor Weight X ± SD | Inhibition Rate % |
|---|---|---|---|---|---|---|
| β-Elemene | 60 | it × 10 qd | 6/5 | 18.0 18.7 | 0.68 ± 0.19*** | 63.24 |
| β-Elemene | 30 | it × 10 qd | 6/6 | 18.1 19.3 | 0.90 ± 0.17*** | 51.35 |
| β-Elemene | 15 | it × 10 qd | 6/6 | 18.3 19.9 | 1.15 ± 0.33*** | 37.83 |
| Pos. Cont. VM-26 | 60 | it × 10 qd | 6/6 | 18.4 19.0 | 0.72 ± 0.12*** | 61.08 |
| Neg. Cont. | 5 mg | ip × 10 qd | 6/5 | 18.1 18.4 | 0.25 ± 0.08*** | 86.49 |
| β-Elemene | Solvent | it × 10 qd | 12/12 | 18.2 19.8 | 1.85 ± 0.19 | |

***$P < 0.01$, compared with negative control group

Intravenous injection of (−)-beta-Elemene at 12.5, 25, and 50 mg/kg, twice a day for 10 days can inhibit 1) human breast cancer (Cap-37) growth in xenographed mice to 36.09, 45.31, and 51.33%; 2) human colon cancer (HCT-8) growth in xenographed mice to 38.32, 49.49, and 57.15%; 3) human prostate cancer (C-3M) growth in xenographed mice to 27.95, 34.78, and 46.58%; 4) human ovary cancer (ao10/17) growth in xenographed mice to 28.28, 35.03, and 44.14%. These experiments have all been repeated.

Materials:

Tested Drug: (−)-beta-Elemene injection (10 mg/ml) and control blank emulsion solution.

Solvent: Control blank emulsion solution.

Positive control: Cyclophosphamide (CTX), Injection, Made by Shanghai Hualian Pharmaceutical Co., i.p. (injection via stomach), once per day, seven days continuously. Tumor Source: 1) human ovary cancer ao10/17, 2) human prostate cancer PC-3M, 3) human lung cancer A549, 4) human liver cancer QGY, 5) human colon cancer HCT-8, and 6) human breast cancer Bcap-37, 7) human glioma SHG422, 8) mice glioma G422. Cell lines of human glioma SHG44, MGC pancreatic cancer MGC, liver cancer QGY, and Leukemia HL60 were maintained by Shanghai Pharmaceutical Industrial Research Institute.

Animals:

Source: Nude mice, provided by the animal center of Chinese Academy of Sciences, Shanghai site. Quality Certificate: No. 005, Hudong Certificate. Kunming mice: provided by own animal facility. Quality Certificate: No. 107, Hudong Certificate.

Weight: Nude mice, 6 weeks old, 18-20 g.

Sex: Both female and male. Every experiment uses animals from the same sex.

Number of animals: Test group and positive control group each had six nude mice. Each Kunming mice group had 10 mice. There were two negative control groups.

Dosage: β-Elemene injection at 50, 25, and 12.5 mg/kg/time.

Drug Protocol: Intravenous injection (i.v.), twice a day, 10 days continuously. All 20 times i.v. injection.

Control Experiment: The blank emulsion solution volume given to the negative control group was the same as that to the test groups. The protocol was twice a day, i.v., 10 days continuously. CTX was given to positive control group at 30 mg/kg each time, once per day, seven days continuously. Mitomycin C (MMC) injection from Xiehe Fermentation Industrial Co. was used as positive control for in vitro experiments.

In vivo Experiments:

Xenograph under the skin of mice armpit: In cell culture hood (no bacteria environment), tumor source ($1 \times 10^7$/ml cell solution, 0.2 ml each mouse) was injected under the skin of the armpit of nude mice. On the second day the xenographed mice were treated with β-Elemene drug. The mice were killed after 3 weeks. Tumor in each mouse was taken out and weighed. The tumor inhibition rate was calculated using the following formula:

$$\text{Inhibition Rate\%} = [(\text{Average tumor weight from negative control group} - \text{Average tumor weight in test group})/\text{Average tumor weight from negative control groups}] \times 100$$

Xenograph models with human tumor sources were carried out using the same procedure. But food, pad, cage, and appliance were sterilized before use. Nude mice grew on the cengliu rack.

Mice model with tumor xenographed in mice brain: Glioma cell line G-422 or SHG44 (log phase) were diluted to $2 \times 10^7$/ml in cell culture hood (no bacteria environment). Each mouse was injected with 0.05 ml of tumor cell in its brain. On the second day the xenographed mice were treated with β-Elemene drug. The survival time of these mice was recorded in the next 30 days. The life extension was calculated using the following formula:

$$\text{Life Extension Rate} = [(\text{Average survival days of control group} - \text{Average survival days of test group})/\text{Average survival days of control group} \times 100$$

Results:

The tumor inhibition rate on A549 lung cancer xenograph models using β-Elemene at 50, 25, and 12.5 mg/kg/time, iv×10 bid was 43.08%, 40.0%, and 31.28% respectively.

TABLE 6

Efficacy of (−)-beta-Elemene, human lung cancer A549 (xenograph under armpit skin)

| Sample | Dose mg/kg/time | Protocol | No. of Animals (No.) Beginning/End | Animal Weight (g) Beginning/End | Tumor Weight (g) $\bar{X} \pm SD$ | Inhibition Rate % |
|---|---|---|---|---|---|---|
| β-Elemene | 50 | iv × 10 bid | 6/6 | 18.8/23.0 | 1.11 ± 0.08*** | 43.08 |
| β-Elemene | 25 | iv × 10 bid | 6/6 | 19.1/23.3 | 1.17 ± 0.09*** | 40.00 |
| β-Elemene | 12.5 | iv × 10 bid | 6/6 | 18.5/23.5 | 1.34 ± 0.10*** | 31.28 |
| CTX | 30 | ip × 7 qd | 6/6 | 19.0/20.8 | 0.29 ± 0.07*** | 85.13 |
| Neg. Cont. | Solvent | iv × 10 bid | 12/12 | 18.8/24.2 | 1.95 ± 0.15 | |

***$P < 0.01$, compared with negative control.

The tumor inhibition rate on QGY liver cancer xenograph models (same protocol as above) was 45.89%, 37.20%, and 30.92%, respectively.

TABLE 7

Efficacy of β-Elemene, human liver cancer QGY (xenograph under armpit skin)

| Sample | Dose mg/kg/ time | Protocol | Animal No. (No.) Beginning/End | Animal Weight (g) Beginning/End | Tumor Weight (g) $\overline{X} \pm SD$ | Inhibition Rate % |
|---|---|---|---|---|---|---|
| β-Elemene | 50 | iv × 10 bid | 6/6 | 19.0/22.2 | 1.12 ± 0.19*** | 45.89 |
| β-Elemene | 25 | iv × 10 bid | 6/6 | 18.2/22.7 | 1.30 ± 0.18*** | 37.20 |
| β-Elemene | 12.5 | iv × 10 bid | 6/6 | 18.5/23.0 | 1.43 ± 0.12*** | 30.92 |
| CTX | 30 | ip × 7 qd | 6/6 | 18.5/19.8 | 0.22 ± 0.12*** | 89.37 |
| Neg. Cont. | solvent | iv × 10 bid | 12/12 | 18.3/22.8 | 2.07 ± 0.20 | |

***$P < 0.01$, compared with negative control.

The tumor inhibition rate on ao10/17 ovary cancer xenograph models (same protocol as above) was 46.42%, 36.25%, and 31.08%, respectively.

TABLE 8

Efficacy of β-Elemene, human breast cancer ao10/17 (xenograph under armpit skin)

| Sample | Dose mg/kg/ time | Protocol | Animal No. (No.) Beginning/End | Animal Weight (g) Beginning/End | Tumor Weight (g) $\overline{X} \pm SD$ | Inhibition Rate % |
|---|---|---|---|---|---|---|
| β-Elemene | 50 | iv × 10 bid | 6/6 | 18.2/23.0 | 0.643 ± 0.1*** | 46.42 |
| β-Elemene | 25 | iv × 10 bid | 6/6 | 18.7/23.0 | 0.765 ± 0.1*** | 36.25 |
| β-Elemene | 12.5 | iv × 10 bid | 6/6 | 18.7/23.0 | 0.827 ± 0.06*** | 31.08 |
| CTX | 30 | ip × 7 qd | 6/6 | 18.8/19.7 | 0.15 ± 0.08*** | 87.50 |
| Neg. Cont. | solvent | iv × 10 bid | 12/12 | 18.5/23.5 | 1.20 ± 0.11 | |

***$P < 0.01$, compared with negative control group.

The tumor inhibition rate on PC-3M prostate cancer xenograph models (same protocol as above) was 46.58%, 34.78%, and 27.95%, respectively.

TABLE 9

Efficacy of β-Elemene, human prostate cancer PC-3M (xenograph under armpit skin)

| Sample | Dose mg/kg/ time | Protocol | Animal No. (No.) Beginning/End | Animal Weight (g) Beginning/End | Tumor Weight (g) $\overline{X} \pm SD$ | Inhibition Rate % |
|---|---|---|---|---|---|---|
| β-Elemene | 50 | iv × 10 bid | 6/6 | 18.8/23.8 | 0.86 ± 0.12*** | 46.58 |
| β-Elemene | 25 | iv × 10 bid | 6/6 | 18.6/24.0 | 1.05 ± 0.07*** | 34.78 |
| β-Elemene | 12.5 | iv × 10 bid | 6/6 | 18.8/23.8 | 1.16 ± 0.12*** | 27.95 |
| CTX | 30 | ip × 7 qd | 6/6 | 18.5/20.0 | 0.205 ± 0.1*** | 87.27 |
| Neg. Cont. | solvent | iv × 10 bid | 12/12 | 18.6/24.3 | 1.61 ± 0.10 | |

***$P < 0.01$, compared with negative control group.

The tumor inhibition rate on HCT-8 colon cancer xenograph models (same protocol as above) was 54.20%, 46.01%, and 35.10%, respectively.

TABLE 10

Efficacy of β-Elemene, human colon cancer HCT-8
(xenograph under armpit skin)

| Sample | Dose mg/kg/ time | Protocol | Animal No. (No.) Beginning/End | Animal Weight (g) Beginning/End | Tumor Weight (g) $\overline{X} \pm SD$ | Inhibition Rate % |
|---|---|---|---|---|---|---|
| β-Elemene | 50 | iv × 10 bid | 6/6 | 18.5/23.8 | 0.655 ± 0.08*** | 54.20 |
| β-Elemene | 25 | iv × 10 bid | 6/6 | 19.2/24.0 | 0.772 ± 0.05*** | 46.01 |
| β-Elemene | 12.5 | iv × 10 bid | 6/6 | 19.0/23.8 | 0.928 ± 0.07*** | 35.10 |
| CTX | 30 | ip × 7 qd | 6/6 | 19.0/19.5 | 0.170 ± 0.08*** | 88.11 |
| Neg. Cont. | solvent | iv × 10 bid | 12/12 | 19.1/24.5 | 1.43 ± 0.12 | |

***P < 0.01, compared with the negative control group.

The tumor inhibition rate on Bcap-37 breast cancer xenograph models (same protocol as above) was 48.08%, 43.23%, and 33.08%, respectively.

TABLE 11

Efficacy of β-Elemene, human breast cancer Bcap-37
(xenograph under armpit skin)

| Sample | Dose mg/kg/ time | Protocol | Animal No. (No.) Beginning/End | Animal Weight (g) Beginning/End | Tumor Weight (g) $\overline{X} \pm SD$ | Inhibition Rate % |
|---|---|---|---|---|---|---|
| β-Elemene | 50 | iv × 10 bid | 6/6 | 19.3/23.8 | 0.675 ± 0.10*** | 48.08 |
| β-Elemene | 25 | iv × 10 bid | 6/6 | 19.5/23.3 | 0.738 ± 0.07*** | 43.23 |
| β-Elemene | 12.5 | iv × 10 bid | 6/6 | 18.7/23.8 | 0.870 ± 0.04*** | 33.08 |
| CTX | 30 | ip × 7 qd | 6/6 | 19.3/20.0 | 0.205 ± 0.12*** | 84.23 |
| Neg. Cont. | solvent | iv × 10 bid | 12/12 | 19.1/24.0 | 1.30 ± 0.13 | |

***P < 0.01, compared with the negative control.

Note: In Example 23, β-Elemene is (−)-beta-Elemene.

General Pharmacology Studies

According to general pharmacology studies, intravenous slow injection of (−)-beta-Elemene injection product at 20, 40, and 80 mg/kg could clearly slow down beagle dog's heart beat, even 2 hours after injection. 40 and 80 mg/kg group extend Q-R interval. 80 mg/kg group reduced systolic pressure. Thus the results indicate that (−)-beta-Elemene injection can inhibit heart function, but does not affect electrocardiogram and breathing. (−)-beta-Elemene injection additionally affects the coordination ability of mice.

Example 24

Toxicity Experiments Using (−)-beta-Elemene
Acute Toxicity Studies

The Toxicology Department of Shanghai Pharmaceutical Industry Research Institute conducted this study. Table 12 gives the $LD_{50}$ of β-Elemene Emulsion, 0.5% as determined in rodents

TABLE 12

(−)-beta-Elemene Emulsion, 0.5%, $LD_{50}$ in rodents

| Route of Administration | $LD_{50}$ (mg/kg) |
|---|---|
| Intraperitoneal (i.p.) | >500 |
| Intravenous (i.v.) | 190 |

No significant clinical symptoms were observed among surviving animals. Most deaths occurred within 24 hours of drug administration. The clinical signs of toxicity were difficulty breathing, vomiting, and diarrhea. No apparent organ damage was observed among the dead animals.

Chronic Toxicity Studies

Two chronic toxicity studies were conducted at The Toxicology Department of Shanghai Pharmaceutical Industry Research Institute, one on Beagle dogs and the other on rats. In Beagle dogs study, three groups of Beagle dogs (n=6 per group) were given (i.v.) 15, 30, or 75 mg/kg/d (iv.) of β-Elemene for 28 days consecutively. High dose group experienced nausea, vomiting, appetite loss, weight loss, saliva dripping and other side effects. Some of the biochemical parameters were changed in high dose group. No significant pathology changes related to drug were observed in low and medium dose groups. In 15 mg/kg group, there was some irritation at local injection site, and no other symptoms. Thus 15 mg/kg was considered non-toxic dose.

In the Rat study, three groups of rats (n=20 per group, half male and half female) were given (i.p.) 7.5, 15, or 30 mg/kg/d of β-Elemene for 28 days consecutively. Six rats in high dose group died. Blood (40-100 ml) was observed in the stomach of these rats. Ascites were developed in all animals in the medium and high dose groups. Ascites were not completely absorbed during 4 weeks without drug intake. No significant changes were observed in the low dose group and in the two control groups, 10% glucose group and placebo emulsion group. Blood and serum biochemistry experiments showed that rats in medium and high dose groups experienced anemia, white blood cell increase. During recovery stage, abnormal AST and ALT levels were observed in some few rats in the medium and high dose groups. Histology study indicated that membrane significantly thickened to some extent and brown particles precipitated in abdominal cavity, pelvic cavity, and trachea of the rats in the medium and high dose groups. Inflammation was observed in some organs of the rats in the medium and high dose groups. The accumulated toxicity of β-Elemene (via i.p.) was not severe, except irritation at local injection site. The safe dose was 7.5 mg/kg/d.

Example 25

Beta-Elemene (2% Emulsion)'s Efficacy Against Brain Tumor in Human Patients

Beta-Elemene drug has significant clinical benefit for brain tumor patients. In a clinical trial experiment conducted by Yuanda, Elemene drug is injected intra-arterially or intravenously (i.v.). The clinical trial was conducted from March 1999 to April 2001 at Chinese FDA designated hospitals.

Among 39 glioblastoma patients in the trial, complete response (CR) is 5%, and partial response (PR) is 31%. Thus the overall tumor response rate is 36%. TEMODAR only has a CR+PR rate of 20%. In addition, 90% of the patients are relieved of the following symptoms: dizziness, headache, speech impairment, neurological dysfunction, and paralysis. Several patients complained of slight itching, which was relieved by hot patches. No allergic reactions were observed. No adverse reactions by liver, kidney, heart, stomach and GI tract, nerve system, and etc. No patient experienced severe lethal reactions. No vomiting or hematological abnormalities were observed.

| | |
|---|---|
| Protocol Title: | Treatment of the Phase II Malignant Intracranial Tumor by 2% Elemene Injection Solution |
| Test Drug: | Elemene Injection Solution, 2% |
| Indication: | Malignant Intracranial Tumors |
| Sponsor: | Dalian Medical Pharmaceutical Science Institute Dalian Yuanda Pharmaceuticals, Ltd. Dalian, China |
| Charge of Project: | Mr. Hai Xu |
| Document type: | Clinical Study Report |
| Development phase: | Phase II (China) |
| Study start date: | April, 1999 |
| Study completion date: | May 25, 2001 |
| Test Drug: | Elemene Injection Solution, 2% |
| Indication: | Malignant Intracranial Tumors |
| Sponsor: | Dalian Medical Pharmaceutical Science Institute Dalian Yuanda Pharmaceuticals, Ltd. Dalian, China |
| Investigators: | Wang Yunjie, Yao Changyi, Gong Maoqing, Liang Chuansheng, Bian Wei, Zhen Wei, Liu Dehuan Zhang Yu, Hou Jusheng, Zhao Jinbo |
| Investigative centers: | Charge Unit for clinical study: No. 1 Affiliated Hospital of China Medical University Neurosurgery of No. 1 Affiliated Hospital of China Medical University Tumor Department of No. 2 Affiliated Hospital of China Medical University Neurosurgery of No. 1 Affiliated Hospital of Dalian Medical University |
| Study Period: | April, 1999-May, 2001 |
| Objectives: | To evaluate the safety and efficacy of Elemene Injection, 2% in the treatment of primary and metastatic brain tumors |
| Study design: | Prospective, single arm, multicenter study |
| Number of Patients: | 61 treated (65 enrolled, 4 withdrew) |
| Demographics: | Gender |
| | Male 37 |
| | Female 24 |
| | Age (yr) mean (range) 48 (8 to 79) |
| Diagnosis (inclusion): | Patients who were confirmed to have primary or metastatic brain tumor, by either pathological record or clear CT/MRI images Patient with tumor progression at least 4 weeks after surgery or radiation treatment Patients for whom initial or further surgery and/or radiation treatment were not appropriate Patients with expected survival time greater than 3 months Patients between 8 and 79 years of age |
| Test Drug: | Elemene Injection Solution, 2%, 200 ml/ampoule, Sanction No. 990622 and No. 990715 |
| Dosage: | 1000 mg per day |
| Route of Administration: | Day 1: 600 mg elemene in 60 mL 10% glucose with 2 mg dexamethasone, IC injection (common carotid artery ipsilateral to unifocal lesions), followed by 400 mg elemene in 500 mL 10% glucose as slow IV infusion Day 2: 1000 mg elemene in 1000 mL 10% glucose by slow IV infusion For multifocal lesions, IC injections were made on alternate sides on the days for carotid administration. For brain stem and subtentorial lesions, drug administration was mainly by the intravenous route over 5-10 hours. Once or twice a week, a 600 mg elemene dose in 10% glucose |

|  |  |
|---|---|
| | solution was administered by femoral artery cannulation via the vertebral artery, if possible. |
| | For suprtentorial lesiosn with obvious cystic changes, local injection into cysts was sometimes performed by drawing out cystic fluid under CT/MRI guidance and replacing the volume with 2% elemene solution |
| | Infusion of 200 mL of mannitol, 20% ½ to 1 hour before elemene infusion was permitted to improve penetration of the blood-brain-barrier. |
| Duration of Treatment: | 20-30 days |
| Procedures: | MRI scans were performed at baseline before study drug administration and at 8 weeks, (4 weeks after the end of study drug administration) Scans were performed using mid- and high-field magnets (1.0-1.5 T). Sagittal T1W, axial double-echo, and pre- and post-gadolinium axial T1W and post-gadolinium coronal T1W images were acquired. The axial scans were to image both the anterior and posterior commissures (along the AC-PC line) and cover the entire brain. Coronal scans were required to cover the tumor. The post-gadolinium series were acquired immediately after intravenous infusion of 0.1 mmol/kg gadolinium. Axial scans were to comprise 12 or more scans to encompass the intracranial contents from the cranial base to the convexity using 5 mm contiguous cuts. |
| | Tumor Size Measurement: Tumor size was measured via CT/MRI at the baseline and at Week 8, four weeks after the last dosing day. Tumor size (volume) was defined as one half of the product of the measures of X-Y-Z dimensions. In patients with multiple tumors, total tumor size was the sum of all individual tumors for an individual patient. |
| Criteria for Evaluation: | Response rates: change in tumor size determined by pre- and post-treatment CT/MRI scans. The following WHO classifications of tumor response were used: |
| Efficacy: | CR: Complete response, no detectable tumor |
| | PR: Partial response, total tumor volume reduced from baseline by over 50% |
| | MR: Moderate response, total tumor volume reduced from baseline by 25-50% |
| | SD: Stable disease, total tumor volume either reduced or increased from baseline by <25%, no new lesions |
| | PD: Progressive disease, total tumor volume increased from baseline by >25% or new lesions appeared |
| | Disease Specific Symptoms assessed as absent or present |
| Safety: | Liver and kidney functions assessed at the baseline and Week 7. |
| | Complete blood counts (CBC: hemoglobin, RBC, WBC, lymphocyte, neutrophil, and platelet counts) at baseline and Weeks 1, 2, 3, and 7. |
| | Adverse experiences |

Results:

| Efficacy | There was a significant decrease from baseline in mean and median tumor size at 8 weeks. |
|---|---|

Elemene Injection, 2%, Prospective Clinical Study:
Change From Baseline in Mean and Median Tumor
Size at 8 Weeks

| | Tumor Size ($cm^3$) N = 61 | |
|---|---|---|
| Time | mean | median |
| Baseline | 40.88 | 29.70 |
| Treatment Week 8 | 20.70[1] | 14.40[1] |

[1] These differences were statistically significant ($p \leq 0.05$). Slightly more than 44% of patient results met the criteria for complete or partial response.

Elemene Injection, 2%, Prospective Clinical Study
Response Rates by WHO Classification of
Response

| Response category | All Evaluable subjects[1] Response |
|---|---|
| Overall response rate (CR + PR) | 27 (44.3) |
| CR | 8 (13.1) |
| PR | 19 (31.1) |
| MR | 11 (18.0) |
| MR | 11 (18.0) |

| | |
|---|---|
| SD | 20 (32.8) |
| PD | 3 (4.9) |
| Any degree of tumor reduction | 41 (67.2) |

[1] All subjects with both pre-treatment and post-treatment CT/MRI

Overall, both primary and metastatic tumors responded to Elemene Injection, 2% treatment Elemene Injection, 2%, Prospective Clinical Study Response Rates by WHO Classification of Response

| Response category | All Evaluable subjects[1]<br>N = 61<br>Response<br>n (%) |
|---|---|
| Overall response rate (CR + PR) | 27 (44.3) |
| CR | 8 (13.1) |
| PR | 19 (31.1) |
| MR | 11 (18.0) |
| SD | 20 (32.8) |
| PD | 3 (4.9) |
| Any degree of tumor reduction | 41 (67.2) |

[1] All subjects with both pre-treatment and post-treatment CT/MRI

The improvements over the baseline in disease specific symptom were clinically significant.

Elemene Injection, 2%, Prospective Clinical Study: Change in Incidence of Disease Specific Symptoms from Baseline to 8 Weeks

| | Incidence of Specific AE in All Patients N = 61 | | |
|---|---|---|---|
| Symptom | Pre-treatment n(%) | Post-treatment n (%) | p-value |
| Somnolence | 3 | 0 | 0.080 |
| Appetite | 6 | 2 | 0.144 |
| Nausea/Vomiting | 23 | 7 | 0.001* |
| Aphasia | 9 | 5 | 0.256 |
| Seizure | 15 | 5 | 0.015* |
| Headache | 44 | 14 | <0.001* |
| Motor Dysfunction | 36 | 14 | <0.001* |
| Hemiplegia | 20 | 6 | 0.002* |

*indicates statistically significant improvement over baseline.

| | |
|---|---|
| Safety | Laboratory values:<br>There were no clinically meaningful changes from baseline in any hematologic variable. Liver and kidney functions were normal for all patients through the entire study with the exception of two subjects whose ALT values were mildly elevated at the Week 7. These abnormal findings were not considered to be clinically significant by the investigator.<br>Adverse experiences<br>Injection site pain was the most common adverse experience. 92% (56/61) patients had WHO Grade I or II pain after injection: 56% (34/61) had Grade I and 36% (22/61) had Grade II pain. No WHO Grade III or IV AEs were observed. No patient in the study required medication to treat any AEs caused by toxicity. No cytotoxicity, such as neutropenia, thrombocytopenia, infection or gastrointestinal toxicity, was seen. |
| Conclusions: | No drug-drug interactions were reported. No overdoses associated with elemene have been reported.<br>Elemene Injection, 2% is a promising treatment for intracranial malignancies. It has been shown to reduce tumor size and improve survival in patients with primary CNS tumors as well as metastatic tumors. It is generally well tolerated. The lack of system toxicity coupled with potential enhancement of other chemotherapeutic anti-neoplastic agents indicates that Elemene Injection, 2% could provide improved tumor reduction with a better safety profile than that of current chemotherapeutic agents. Elemene Injection, 2% both alone and in combination with other therapeutic agents should be studied further for its use in treatment of intracranial malignancies. Elemene Injection, 2% may also have uses in other types of malignancies. |

Example 26

Beta-elemene (0.5% Emulsion)'s Efficacy Against Lung Cancer

Study 1—Combination Therapy with Injection Emulsion of Elemene and Radiation Therapy in the Treatment of Stage IV Non-small Cell Lung Cancer. Jie Li & Ju-Sheng Hou, The Cancer Hospital of the Second Affiliated Hospital, Dalian Medical University, Dalian, P. R. China.

|  | Combination Therapy | Radiation Therapy |
|---|---|---|
| Patient Information | 30 patients with Stage IV non-small cell lung cancer. | 30 patients with Stage IV non-small cell lung cancer. |
| Dosage | Elemene: 200-600 mg/m$^2$ for 2-4 weeks (in some cases, 6 weeks). Radiation: Total - 40 Gy, 2 Gy per session, 5 times per week. Dosage reduced to 24 Gy if signs of tumor shrinkage are observed. For patients showing signs of metastasis to the bone, 30-40 Gy total therapy is administered at 5 Gy intervals. For patients showing signs of metastasis to the brain, a total dose of 30 Gy is administered at 1.5-2 Gy intervals (an additional 20 Gy is administered if signs of tumor shrinkage are observed). | Radiation: Total - 40 Gy, 2 Gy per session, 5 times per week. Dosage reduced to 24 Gy if signs of tumor shrinkage are observed. For patients showing signs of metastasis to the bone, 30-40 Gy total therapy is administered at 5 Gy intervals. For patients showing signs of metastasis to the brain, a total dose of 30 Gy is administered at 1.5-2 Gy intervals (an additional 20 Gy is administered if signs of tumor shrinkage are observed). |
| Delivery Method | Elemene: Continuous IV drip of Elemene diluted in PBS for 2-4 weeks. Radiation: Co$^{60}$ source. Localized radiation on tumor and/or lymph nodes separately. | Radiation: Co$^{60}$ source. Localized radiation on tumor and/or lymph nodes separately. |
| Efficacy | CR: 6.6% PR: 40% | CR: 0% PR: 23.3% |
| Side Effects | Decreased WBC count: level 1 (30%) and level 2 (3.3%). Two patients dropped out of the study because of reduced WBC counts. Nausea and vomiting: level 1 to 2 (16.7%), level 3 to 4 (3.3%). Pneumonia due to radiation: 10% Phlebitis: 16.7% | Decreased WBC count: level 1 (40%), level 2 (23.3%), level 3 (3.3%). Eight patients dropped out of study due to reduced WBC counts. Nausea and vomiting: level 1 to 2 (20%), level 3 to 4 (6.6%). Pneumonia due to radiation: 10% |

Study 2—Comparative Study on Dual Artery Infusion of Elemene and Chemotherapeutic Agents in the Treatment of Lung Cancer. Xin Li, Shao-Xiong Xu, & Guo-Yan Shang, Department of Radiology, Guiyang Medical College, Guiyang, P. R. China.

|  | Elemene Group | DAI Control Group | BAI Control Group |
|---|---|---|---|
| Patient Information | 30 lung cancer patients infused via DAI, along with Elemene and chemotherapeutic agent. | 30 lung cancer patients infused via DAI, along with chemotherapeutic agent alone. | 30 lung cancer patients infused via BAI, along with chemotherapeutic agent alone. |
| Dosage | Elemene: 500 mg/m$^2$ Standard chemotherapy drugs. | Elemene: 500 mg/m$^2$ Standard chemotherapy drugs. | Elemene: 500 mg/m$^2$ Standard chemotherapy drugs. |
| Delivery Method | 1$^{st}$ treatment via BAI. 2$^{nd}$ to 4$^{th}$ treatment via DAI (half BAI and half PAI) | Same as Elemene Group except that drug mixture did not contain Elemene. | BAI 3-4 times. Drug mixture did not contain Elemene. |
| Efficacy | CR: 10% PR: 73.3% | CR: 6.7% PR: 70% | CR: 3.3% PR: 53.3% |

-continued

|  | Elemene Group | DAI Control Group | BAI Control Group |
|---|---|---|---|
|  | 1 and 2 year survival rate: 73.3% and 60%, respectively. Median survival time: 15 months | 1 and 2 year survival rate: 70% and 33.3%, respectively. Median survival time: 12 months | 1 and 2 year survival rate: 60% and 25%, respectively. Median survival time: 9 months |
| Side Effects | During BAI, patients complained of bronchial irritation, chest pains and coughs. Serious side effects included: anxiety, shortness of breath, cold sweats, breathing difficulties. Patients recovered after slowing injection rate and administration of Lidocain and Dexamethasone. |  |  |

BAI: Bronchial Artery Infusion
PAI: Pulmonary Artery Infusion
DAI: BAI & PAI

Study 3—Studies of Elemene Emulsion in Treating Late Stage Lung Cancer. Jia-liu Zhang, Xue-chang Zhang, & Jing-san Zhang, Department of respiratory system, Kunming No. I People's Hospital. Kunming, P. R. China.

|  | Elemene Group |
|---|---|
| Patient Information | 11 late-stage lung cancer patients injected with Elemene alone. |
| Dosage | One treatment cycle: 400 mg Elemene in 250 ml of 5% GNS everyday for 10 days. One week break. 800 mg Elemene in 500 ml of 5% GNS everyday for 5 days. One week break. 800 mg Elemene in 500 ml of 5% GNS everyday for 5 days. |
| Delivery Method | IV drip. |
| Efficacy | CR: 0% PR: 50% PR (after 1 year): 40% |
| Side Effects | Phlebitis: 18.2%. Relieved by administration of 50 mg of Lidocain by IV before Elemene IV drip. Dexamethasone was also administered by IV after Elemene delivery. In the second treatment cycle, the injection device had to be buried in the vein due to hardening of the vein. |

Study 4—Clinical Trial Observation of Lung Cancer Patients Treated with Elemene Emulsion, Shu-kui Qin, Jun Qian, Lin Wang, & Ze-ming He, Department of Internal Medicine, Cancer Center, Nanjing Ba-yi Hospital, Nanjing, P. R. China

|  | Elemene Therapy (Primary Lung Cancer) | rIL-11 Therapy (Metastatic Lung Cancer) |
|---|---|---|
| Patient Information | 46 patients with median or late stage primary lung cancer | 7 patients with median or late stage metastatic lung cancer |
| Dosage | 400 mg Elemene in 20 ml PBS, once a day, 10 days as a cycle. 3 week break. Repeat once more. | 400 mg Elemene in 20 ml PBS, once a day, 10 days as a cycle. 3 weeks break. Repeat once more. |
| Delivery Method | IV | IV |
| Efficacy | CR: 4.3%, PR: 30.4%. | CR: 0%, PR: 14.3%. |
| Side Effects | No change in liver and kidney function. No change in electrocardiogram. | No change in liver and kidney function. No change in electrocardiogram. |

| | Elemene Therapy (Primary Lung Cancer) | rIL-11 Therapy (Metastatic Lung Cancer) |
|---|---|---|
| | Fever, phlebitis, nausea, breathing irritation. 2 patients: coughed up blood. 1 patient: dramatic platelet decrease and severe bleeding. | Fever, phlebitis, nausea, breathing irritation. Some patients experienced swelling, stuffiness, and heavy breath. The symptoms could be relieved by slowing the injection speed. |

Example 27

Beta-elemene(0.5% Emulsion)'s Efficacy Against Esophagus Cancer and Pancreatic Cancer
Study 5—Clinical Evaluation of Elemene in Treating Esophageal Cancer and Pancreatic Cancer. Shi-yong Yang, Evaluation Group, on Elemene's Clinical Effect to esophagus cancer and pancreatic cancer patients, Xian, P. R. China

| | Esophagus Cancer | Pancreatic Cancer |
|---|---|---|
| Patient Information | 14 esophageal cancer patients. | 28 pancreatic cancer patients. |
| Dosage | 300-600 mg Elemene, 5 days continuously. Repeat treatment once more after 3 weeks. Smallest dosage: 130 mg per session. Largest dosage: 1000 mg per session. Total treatment dosage: 61.9% in 3000-7000 mg range. | |
| Delivery Method | 92.9% IV drip 2 patients - IV under collarbone. | 1 patient - arterial injection under duodenum. |
| Efficacy | CR: 0% PR: 28.57% | CR: 0% PR: 25% |
| Side Effects | According to WHO's evaluation method, in both treatment groups: WBC level: 95.2% normal, 4.8% level I abnormal. Liver function (ALT): 95.2% normal, 2.4% at level I abnormal, 2.4% at level II abnormal. Kidney function (BUN): 100% normal. | |

Example 28

Beta-elemene(0.5% Emulsion)'s Efficacy Against Gastrointestinal Tract Tumors
Study 6—Treatment of 30 Patients with Malignant Gastrointestinal Tract Tumors through Multi-method Delivery of Elemene. Qing-zhen Zhang, Li-xian Cu, & Xian-jun Zhu, Zhang-qiu People's Hospital, Zhang-qiu, P. R. China

| | Elemene Group | Chemotherapy Group |
|---|---|---|
| Patient Information | 30 patients with gastrointestinal tract tumors treated with Elemene alone. | 28 patients with gastrointestinal tract tumors treated with DPP and 5-FU. |
| Dosage | Elemene: 300 mg in 500 ml glucose solution once a day for 10 days continuously. Additional oral intake of Elemene (100 mg) with 5 mg Dexamethasone and 2 ml Pu-lu-ka-yin in 10% glucose solution. Treatment cycle was repeated after 3 weeks. | Chemotherapy: 40 mg DPP on days 1, 3, 8 and 10. 400 mg 5-FU from day 1 to 5. Treatment cycle was repeated after 3 weeks. |
| Delivery Method | IV drip | DPP by IM, 5-FU by IV |
| Efficacy | CR: 36.6% PR: 40% | CR: 17.9% PR: 28.5% |
| Side Effects | Fever: 2-6 hours after Elemene injection, body temperature ~38 C. Patients recovered within one week. Oral intake of Elemene did not result in adverse side effects except for localized light pains. | |

Study 7—Clinical Effects of Elemene Emulsion in the Treatment of Late-Stage Gastrointestinal Tract Tumors through Induction of Stomach Ascites. Gui-fen Niu & Nan-sheng Cheng, Department of Digestive Systems, Suzhou No.2 People's Hospital, Suzhou, P. R. China

|  | Elemene Group |
| --- | --- |
| Patient Information | 30 patients with late-stage gastrointestinal tumors |
| Dosage | 400 mg Elemene, 1-2 times each week, for 3 weeks. After 4 weeks, repeat the treatment cycle. |
| Delivery Method | Stomach ascites was first aspirate. Next, 20 ml 2% Lidocain was injected into stomach cavity, followed by 250 ml 0.9% PBS, and finally, 400 mg Elemene in 500 ml 0.9% PBS. This is called induced stomach ascites, which will be absorbed in 48 hours. |
| Efficacy | CR: 69.7% <br> PR: 21.7% |
| Side Effects | Abdominal distension due to injection of drugs. <br> Light stomach pain and stuffiness in the chest: 30%. <br> Nausea and lack of appetite: 16.7%. <br> No obvious changes in blood statistics <br> No impairment of liver, kidney and cardiovascular function (measured by electrocardiograms). |

Example 29

Beta-elemene(0.5% Emulsion)'s Efficacy Against Colorectal Cancer
Study 8—Clinical Effects Analysis of 65 Cases of Colorectal Cancer using Elemene Emulsion. Gao Xiang, Xue-zai Chen, & Gui-feng Chen, Department of Oncology, Nanpin No. 1 Hospital, Nanpin, Fujian Province, P. R. China

|  | Elemene Group |
| --- | --- |
| Patient Information | 65 colorectal cancer patients. All patients had exercised surgical removal of colon between 6 months to 2 years ago. |
| Dosage | 400 mg Elemene, 4 times each week, for 6 months. |
| Delivery Method | Elemene was delivered (in the course of 1-2 hours) through the anus using inflatable devices which surround the drug delivery tube. |
| Efficacy | CR: 4.6% <br> PR: 69.2% |
| Side Effects | Few side effects (no details). |

Study 9—Short-term Clinical Effect Observation of Late-Stage Colorectal Cancer Cases Treated by Elemene Emulsion through Conservative Enema. Qun-xiong Pan, & Jie-ji Guo, Department of Surgery, Quan-zhou No.1 Hospital, Quan-zhou, Fujian Province, P. R. China

|  | Elemene Group | 5-FU Group |
| --- | --- | --- |
| Patient Information | 17 late-stage colorectal cancer patients treated with Elemene alone. | 14 late-stage colorectal cancer patients treated with 5-FU. |
| Dosage | Elemene: 200 mg in 40 ml PBS (incubated in colon for 2 hours) twice a day for 10 days continuously. | 5-FU: 500 mg 5-FU in 40 ml PBS (incubated in colon for 2 hours) twice a day for 10 days. |
| Delivery Method | Enema method | Enema method |
| Efficacy | CR: 58.8% <br> PR: 23.5% | CR: 57.1% <br> PR: 21.4% |
| Side Effects | No damage to heart, liver or kidney. <br> No bone marrow inhibition. <br> No obvious reaction in digestive system. |  |

Study 10-18 Cases with Colon Obstruction after Colon Cancer Surgery Treated with Elemene Emulsion by Intravenous Injection Under Collarbone, Rui-lan Li, & Zhong-de Liu, Hunan Herbal Medicine Tumor Hospital, Changsha, Hunan Province, P. R. China

|  | Elemene Therapy |
| --- | --- |
| Patient Information | 18 patients with colon obstruction after colon cancer surgery |
| Dosage | 400 mg Elemene in 100 ml PBS, once a day, 10 days as a treatment cycle. After 3 weeks of break, repeat the same cycle. |
| Delivery Method | IV injection under collarbone. |
| Efficacy | After 1 treatment cycle <br> CR: 27.8% (no pain), PR: 44.4% (pain is relieved) <br> After 2 treatment cycle <br> CR: 22.2% (no colon blockage), PR: 44.4% (reduced colon blockage) |
| Side Effects | Fever (>38 C.): 38.9%. Some over 39 C. <br> Nausea and loss of appetite: 16.7%. <br> No adverse effect on blood, liver and kidney function, and electrocardiogram |

Example 30

Beta-Elemene(0.5% Emulsion)'s Efficacy Against Stomach Cancer
Study 11—Observation of Malignant Stomach Tumors Treated with Elemene Emulsion Through the Intestine, Jin-lian Zhang, & Mei-xia Wu, Fujian Longyan District No. 2 Hospital, Longyan, Fujian Province, P. R. China

|  | Elemene Therapy (Through Intestine) | Elemene Therapy (IV) |
| --- | --- | --- |
| Patient Information | 15 malignant stomach tumor patients | 16 malignant stomach tumor patients |
| Dosage | 300-400 mg Elemene in 100 ml 10% GS, 5-7 times per cycle. Two cycles. | 300-400 mg Elemene in 100 ml 10% GS, 5-7 times per cycle. Two cycles. |
| Delivery Method | Intestinal injection (tube size 10-15 cm) at 60-80 drops per minute. Elemene left in intestine for 2-4 hours after injection. | IV |
| Efficacy | CR: 6.7%, <br> PR: 33.3%. | CR: 0%, <br> PR: 31.5%. |
| Side Effects | WBC decrease: 26.7% at level I, 13.3% at level II | WBC decrease: 37.5% at level I, 6.25% at level II |

-continued

| Elemene Therapy (Through Intestine) | Elemene Therapy (IV) |
|---|---|
| Frequent bowel movement: 2-4 times a day, recover on the second day, feces has liquid-like consistency. Hair loss, loss of appetite, and nausea. | Phlebitis: 100%. Hair loss, loss of appetite, and nausea. |

Example 31

Beta-elemen(0.5% Emulsion)'s Efficacy Against Primary Liver Cancer
Study 12—Clinical Trial Summary on Primary Liver Cancer Patients Treated with Elemene Emulsion through Hepatic Arterial Injection, Li-seng Xiao, & Wei-ming Zhu, Wuxi No.4 People's Hospital, Wuxi, Jiangsu Province, P. R. China

| | Elemene Therapy |
|---|---|
| Patient Information | 71 patients with primary liver cancer |
| Dosage | 400-1000 mg (mainly 600 mg) Elemene. |
| Delivery Method | Injection through hepatic artery and embolism. |
| Efficacy | CR: 2.8%, PR: 53.5%. |
| Side Effects | Fever: Some. Pain: 23.9% (level I), 5.6% (level II), 1.4% (level III). 1 patient: after treatment, experience shortness breath, stuffiness, swelling, palpitations, high blood pressure. These symptoms lasted 30 minutes and disappeared after proper treatment. |

Example 32

MTT assay on Elemene Derivative LR1 to LR10's Anti-tumor Activity

Using the same MTT assay protocol detailed in Example 22, we have detected IC50 of LR1 to LR10 in inhibiting human glioma cell line growth. The table is as below.

TABLE 13

Cytotoxicity efficacy of elemene analogs demonstrated by IC50 (ug/ml) in human glioma cells

| | Lr-1 | Lr-2 | Lr-3 | Lr-4 | Lr-5 | Lr-6 | Lr-7 | Lr-8 | Lr-9 | Lr-10 | (−)-beta-elemene |
|---|---|---|---|---|---|---|---|---|---|---|---|
| 24 hr | 176.24 | 131.78 | >200 | >200 | >200 | >200 | >200 | 106.2 | >200 | >200 | 95.52 |
| 48 hr | 163.23 | 89.60 | >200 | >200 | >200 | >200 | >200 | 105.2 | >200 | >200 | 88.48 |
| 72 hr | 133.13 | 90.90 | >200 | >200 | >200 | >200 | >200 | 103.3 | >200 | >200 | 93.34 |

TABLE 14

Cytotoxicity efficacy of elemene analogs demonstrated by IC50 (ug/ml) in three human brain tumor cells

| | Cell lines | IC50 (μg/ml) | | |
|---|---|---|---|---|
| Test Article | (Brain Tumor) | 24 h | 48 h | 72 h |
| (−)-beta-elemene | A172 | 88 | 84 | 80 |
| Lr-1 | A172 | 106 | 94 | 90 |
| Lr-2 | A172 | 122 | 96 | 65 |
| Lr-3 | A172 | >140 | 134 | 106 |
| (−)-beta-elemene | U87 | 100 | 108 | 108 |

TABLE 14-continued

Cytotoxicity efficacy of elemene analogs demonstrated by IC50 (ug/ml) in three human brain tumor cells

| | Cell lines | IC50 (μg/ml) | | |
|---|---|---|---|---|
| Test Article | (Brain Tumor) | 24 h | 48 h | 72 h |
| Lr-1 | U87 | 98 | 94 | 89 |
| Lr-2 | U87 | 90 | 94 | 87 |
| Lr-3 | U87 | 118 | >120 | 120 |
| (−)-beta-elemene | STTG1 | 112 | 115 | 112 |
| Lr-1 | STTG1 | 108 | 98 | 94 |
| Lr-2 | STTG1 | 112 | 98 | 97 |
| Lr-3 | STTG1 | 108 | >120 | 110 |

Example 33

The effect of (−)-beta-Elemene (2% Emulsion) as control, and (−)-beta-elemenol, (−)-beta-elemenal, and (−)-beta-elemene fluoride (called test articles for simplicity in the following paragraph) on anti-tumor activity in human carcinoma cells was determined by the MTT survival assay, or using a commercial MTT assay kit (Cell Titer 96 Aqueous One Solution Cell Proliferation Assay; Promega Corporation, Madison, Wis.) according to the manufacturer's instructions. The MTT assay is a commonly used method in evaluation of cell survival, based on the ability of viable cells to convert MTT, a soluble tetrazolium salt [3-(4,5-dimethylthuazole-2-yl)-2,5 diphenyl tetrazolium bromide], into an insoluble formazan precipitate, which is quantitated by spectrophotometry following solubilization in dimethyl sulfoxide (DMSO).

In brief, carcinoma cells treated with test articles alone, in 96-well tissue culture dishes were incubated with MTT (2 μg/ml) for 4 h. The cells were then solubilized in 125 μl of DMSO and absorbance readings were taken using a 96-well Opsys MRI Microplate Reader (ThermoLabsystems; Chantilly, Va.). The amount of MTT dye reduction was calculated based on the difference between absorbance at 570 nm and at 630 nm. Cell viability in treated cells was expressed as the amount of dye reduction relative to that of untreated control cells. The wells that contained only medium and 10 μl of MTT were used as blanks for the plate reader. Three sets of experiments were performed in 8-12 wells for each treatment, shown in Table 1 below.

TABLE 15

Cytotoxicity efficacy of elemene analogs demonstrated by IC50 (detected by MTT-assay, $2 \times 10^4$ cells/ml)

| | Cell line | IC50 (μg/ml) | | |
|---|---|---|---|---|
| Test Article | (lung cancer) | 24 h | 48 h | 72 h |
| (−)-beta-elemene | H460 | 89.5 | 70.6 | 68.2 |
| (−)-beta-elemenol | H460 | 111.0 | 69.0 | 74.5 |

TABLE 15-continued

Cytotoxicity efficacy of elemene analogs demonstrated by IC50 (detected by MTT-assay, $2 \times 10^4$ cells/ml)

| Test Article | Cell line (lung cancer) | IC50 (μg/ml) | | |
|---|---|---|---|---|
| | | 24 h | 48 h | 72 h |
| (−)-beta-elemenal | H460 | 27.6 | 25.5 | 11.0 |
| (−)-beta-elemene fluoride | H460 | 71.3 | 62.5 | 68.6 |
| (−)-beta-elemene | A549 | 62.0 | 55.6 | 56.4 |
| (−)-beta-elemenol | A549 | 74.0 | 60.1 | 81.0 |
| (−)-beta-elemenal | A549 | 45.6 | 35.0 | 35.0 |
| (−)-beta-elemene fluoride | A549 | 83.0 | 64.5 | 71.4 |

Example 34

Synergistic Effect by Combining (−)-Beta-elemene with Cisplatin

The effect of (−)-beta-Elemene and/or cisplatin on antitumor activity in human carcinoma cells was determined by the MTT survival assay, or using a commercial MTT assay kit (CellTiter 96 Aqueous One Solution Cell Proliferation Assay; Promega Corporation, Madison, Wis.) according to the manufacturer's instructions. The MTT assay is a commonly used method in evaluation of cell survival, based on the ability of viable cells to convert MTT, a soluble tetrazolium salt [3-(4,5-dimethylthuazole-2-yl)-2,5 diphenyl tetrazolium bromide], into an insoluble formazan precipitate, which is quantitated by spectrophotometry following solubilization in dimethyl sulfoxide (DMSO).

In brief, carcinoma cells untreated and treated cisplatin alone, or the combination of (−)-beta-Elemene (at IC20 of each cancer cell line) and cisplatin in 96-well tissue culture dishes were incubated with MTT (2 μg/ml) for 4 h. The cells were then solubilized in 125 μl of DMSO and absorbance readings were taken using a 96-well Opsys MRI Microplate Reader (ThermoLabsystems; Chantilly, Va.). The amount of MTT dye reduction was calculated based on the difference between absorbance at 570 nm and at 630 nm. Cell viability in treated cells was expressed as the amount of dye reduction relative to that of untreated control cells. The wells which contained only medium and 10 μl of MTT were used as blanks for the plate reader. Three sets of experiments were performed in 8-12 wells for each treatment.

TABLE 16

Elemene increases cisplatin cytotoxicity and enhances cisplatin sensitivity in human cancer cells as determined by the MTT assay

| Cancer cell type | Cisplatin $IC_{50}$ (uM) | Cisplatin (uM) + Elemene | DMF |
|---|---|---|---|
| A-172 brain tumor | 24 | 0.25 | 96 |
| U-87 brain tumor | 10 | 1.8 | 5.6 |
| H-460 lung cancer | 80 | 8.0 | 10 |
| H-69 lung cancer | 8.0 | 1.5 | 5.3 |
| MCAS ovarian cancer | 38 | 6.5 | 5.8 |
| T-24 bladder cancer | 32 | 1.2 | 26.7 |
| CCL-2 (Hela) cervical cancer | 27.5 | 3.0 | 9.2 |
| HTB-33 cervical cancer | 32 | 3.8 | 8.4 |
| CCL-222 colon cancer | 32 | 3.5 | 9.1 |
| MCF-7 breast cancer | 28 | 0.38 | 73.7 |
| T47D breast cancer | 31 | 0.25 | 124 |
| DU-145 prostate cancer | 384 | 6.0 | 64 |
| PC-3 prostate cancer | 80 | 8.0 | 10 |

Example 35

In vitro Combination Characterization of the New Antitumor Plant Drug (−)-Beta-elemene with Taxanes Against Human Lung Cancer Combination Effects Evaluated by Synergistic Analysis $$CI = \frac{IC_{50} \text{ Elemene combined}}{IC_{50} \text{ Elemene alone}} + \frac{IC_{50} \text{ Taxane combined}}{IC_{50} \text{ Taxane alone}} \quad (1)$$

$$CI = \frac{IC_{50} \text{ Elemene combined}}{IC_{50} \text{ Elemene alone}} + \frac{IC_{50} \text{ Taxane combined}}{IC_{50} \text{ Taxane alone}} + \frac{IC_{50} \text{ Elemene combined}}{IC_{50} \text{ Elemene alone}} \frac{IC_{50} \text{ Taxane combined}}{IC_{50} \text{ Taxane alone}} \quad (2)$$

It is basically classified as that CI value<1.0 indicates synergism, CI=1.0 additive effect and CI>1.0 antagonism.

The combination effects of (−)-beta-elemene with paclitaxel or docetaxel at higher levels of cytotoxicity (at IC50) on the inhibition of human lung cancer cell proliferation are shown in Table 17. From these data, it can be concluded that either when the mechanisms of drug action were assumed to be mutually exclusive or mutually nonexclusive, CIs for combinations of (−)-beta-elemene with paclitaxel or docetaxel, revealed cytotoxic effects ranging from slight synergism to synergism. Much stronger synergistic effects of combination interactions were observed in P53 mutation and P53 null type cells than in P53 wild type cells. Furthermore, CIs of (−)-beta-elemene with paclitaxel or docetaxel varied depending on the cell types examined. These variations might reflect differences in the way different lung cancer cells handle drug-inflicted damage. However, no obviously differences were noted in the CIs between that obtained with the combinations of (−)-beta-elemene and paclitaxel, and that with the combinations of (−)-beta-elemene and docetaxel in 4 examined cell lines.

TABLE 17

Synergistic analysis on doublet combinations of (−)-beta-Elemene with paclitaxel or docetaxel after 72 hours simultaneously treatments in 4 human lung cancer cell lines

| Cell line | Drug combination | CI* (mean ± SD) | CI** (mean ± SD) |
|---|---|---|---|
| A549 | β-elemene + paclitaxel | 0.70 ± 0.03 | 0.86 ± 0.06 |
| | β-elemene + docetaxel | 0.74 ± 0.06 | 0.88 ± 0.08 |
| H460 | β-elemene + paclitaxel | 0.78 ± 0.15 | 0.89 ± 0.14 |
| | β-elemene + docetaxel | 0.66 ± 0.09 | 0.76 ± 0.11 |
| H23 | β-elemene + paclitaxel | 0.44 ± 0.06 | 0.48 ± 0.09 |
| | β-elemene + docetaxel | 0.49 ± 0.09 | 0.55 ± 0.06 |
| H358 | β-elemene + paclitaxel | 0.49 ± 0.07 | 0.54 ± 0.05 |
| | β-elemene + docetaxel | 0.67 ± 0.09 | 0.78 ± 0.07 |

Doublet combinations of β-elemene with paclitaxel or docetaxel were evaluated in 4 human lung cancer cell lines. CI values are shown for Fa 50 (Fa is defined as the fraction of cells affected, Fa 50 is defined at that point where 50% of the cell were inhibited).
Means ± SD of three independent experiments were provided for all 4 human lung cancer cell lines.
*CI values for mutually exclusive of two combined drugs
**CI values for mutually nonexclusive of two combined drugs Example 36

Effect of 5-Fu Combination with (−)-beta-Elemene on Human Colon Cancer Cells
Discovery:
(1) 5-fu and oxaliplatin combination with (−)-beta-elemene in simultaneous administration produced antagonistic effects in all of 4 colon cancer cells, HCT-116, HCT-15, Caco-2 and Colo 205;

(2) 5-fu combination with (−)-beta-elemene in sequential administration produced antagonistic effects in colon cancer cells, HCT-116, HCT-15, and additive effects or synergistic effects in Caco-2 and Colo 205;
(3) Oxaliplatin combination with (−)-beta-elemene in simultaneous administration produced additive effects or synergistic effects in all of 4 colon cancer cells, HCT-116, HCT-15, Caco-2 and Colo 205.

Cell Culture and Drug Treatment

The HCT-15, HCT-116, Caco-2, Colo 205, HCT-15(+COX-2) human colon cancer cell lines were obtained from the American Type Culture Collection (Manassas, Va.) and grown in RPMI 1640 supplemented with 10% fetal bovine serum. Cells were maintained at 37° C. in a humidified atmosphere including 5% $CO_2$. Cells were seeded 24 h before drug treatment. The effect of (−)-beta-Elemene, and 5-Fu (Sigma) on colon cancer cell lines were studied. Drugs were dissolved in 100% DMSO and then diluted in medium for experiments.

Cell Viability Assays

Cells were seeded at 3000 cells/well on 96-well plates 24h before drug treatment, and then treated with a range of concentrations of (−)-beta-elemene, 5-Fu alone and oxaliplatin for 4, 8, 12, 24, 48, 72 hr; The interactive effects of 5-Fu, oxaliplatin combination with (−)-beta-elemene on colon cancer cell lines, HCT-116, HCT-15, Caco-2, Colo 205 and HCT-15(+COX-2) in simultaneous and sequential administration schedules were investigated, which treated by elemene 160○ g/ml in HCT-116, HCT-15, HCT-15(+COX-2) and (−)-beta-elemene 80○ g/ml in Caco-2, Colo 205 combining with the same concentration of 5-Fu alone and oxaliplatin alone in simultaneous administration for 4, 8, 12, 24, 48, 72 hr, or which treated by (−)-beta-elemene 160○ g/ml for 2, 4, 8, 6, 12, 24, 36 hr, then followed by the same range of concentration of 5-Fu alone for 2, 4, 8, 6, 24, 36 hr in HCT-116 cells and HCT-15 cells, and which treated by elemene80○ g/ml for 2, 4, 8, 6, 12, 24, 36 hr, then followed by the same range of concentration of 5-Fu alone and oxaliplatin alone for 2, 4, 8, 6, 24, 36 hr in Caco-2 cells and Colo 205 cells; Cell viability was assessed by the CellTiter96® AQueous One Soultion Reagent (Promega, Madison, Wis.), contain a novel compound [3-(4,5-dimethylthiazol-2-yl)-5-(3-carboxymethoxyphenyl)-2-(4-sulfophenyl)-2H-tetrazo lium, inner salt; MTS], add the solution to the medium at a final concentration of 1 mg/ml/well, after incubation at 37° C. for 1-2 hr, Absorbance was measured at a wavelength of 490 nm using a 96-well microplate reader (Molecular Devices, Wokingham, United Kingdom).

Results

MTS assay demonstrated that (−)-beta-elemene in combination with 5-FU and oxaliplatin for 4 to 72 hrs according to a simultaneous schedule resulted in antagonistic effects in all of 4 cell lines HCT-116,HCT-15,Caco-2 and Colo 205; Sequential exposure to (−)-beta-elemene for 2, 4, 6, 12 hrs followed by 5-FU for 2, 4, 6, 12 hrs produced synergistic effects and Sequential exposure to (−)-beta-elemene for 24, 36 hrs followed by 5-FU for 24, 36 hrs produce additive effects in Colo 205 and Caco-2 cells; and sequential schedule still results in antagonistic effects in HCT-15 and HCT-116 cells; moreover, sequential exposure to (−)-beta-elemene for 2 to 36 hrs followed by oxaliplatin 2 to 36 hrs produced synergistic effects. In the following tables, (−)-beta-elemene is abbreviated as Elemene.

TABLE 18

Effect of 5-Fu and Oxaliplatin Combination with Elemene in Sequential Administration on Colon Cancer Cells HCT-116 (n = 8)

| Time | IC50 (μg/ml) | | | | |
|---|---|---|---|---|---|
| | Elemene alone | 5-Fu alone | 5-Fu + Elemene (160 μg/ml) | Oxaliplatin alone | Oxaliplatin + Elemene (160 μg/ml) |
| 4 hr | 363 ± 45.9 | 83.3 ± 12.1 | 76.5 ± 21.1 | 373 ± 69.6 | 222 ± 27.5''' |
| 8 hr | 206 ± 24.2 | 43.1 ± 13.1 | 40.3 ± 6.15 | 92.2 ± 15.7 | 67.6 ± 8.06''' |
| 12 hr | 201 ± 12.0 | 21.7 ± 3.70 | 39.1 ± 9.10** | 74.4 ± 6.28 | 53.9 ± 11.6''' |
| 24 hr | 184 ± 26.1 | 11.8 ± 2.54 | 39.5 ± 1.87** | 68.9 ± 7.92 | 48.4 ± 9.40''' |
| 48 hr | 163 ± 21.8 | 7.4 ± 1.82 | 39.4 ± 6.07** | 64.5 ± 7.89 | 38.1 ± 14.9''' |
| 72 hr | 157 ± 22.0 | 4.5 ± 0.74 | 46.8 ± 1.11** | 57.2 ± 10.5 | 33.5 ± 6.74''' |
| 4 hr/24 hr | 230 ± 25.2 | 85.1 ± 8.89 | 83.0 ± 18.46 | 148 ± 13.7 | 105 ± 15.86''' |
| 4 hr/24 hr × 2 | 203 ± 23.1 | 42.7 ± 4.78 | 39.2 ± 8.43 | 106 ± 15.7 | 47.7 ± 8.61''' |
| 4 hr/24 hr × 3 | 165 ± 22.0 | 22.4 ± 8.75 | 18.5 ± 9.58 | 65.7 ± 7.02 | 41.3 ± 9.09''' |

Compared with 5-Fu alone *p < 0.05; **p < 0.01
Compared with oxaliplatin alone ''p < 0.05, '''p < 0.01

TABLE 19

Effect of 5-Fu and Oxaliplatin Combination with Elemene in Sequential Administration on Colon Cancer Cells HCT-15 (n = 8)

| Time | IC50 (μg/ml) | | | | |
|---|---|---|---|---|---|
| | Elemene alone | 5-Fu alone | 5-Fu + Elemene (160 μg/ml) | Oxaliplatin alone | Oxaliplatin + Elemene (160 μg/ml) |
| 4 hr | 229 ± 26.9 | 93.0 ± 9.11 | 86.0 ± 11.7 | 28.4 ± 6.80 | 6.91 ± 3.54''' |
| 8 hr | 215 ± 34.1 | 68.1 ± 7.63 | 62.0 ± 12.5 | 25.7 ± 5.61 | 5.11 ± 1.75''' |
| 12 hr | 202 ± 21.8 | 52.1 ± 5.09 | 127 ± 23.1** | 19.3 ± 3.21 | 4.02 ± 4.01''' |
| 24 hr | 194 ± 19.3 | 26.5 ± 13.9 | 67.4 ± 19.6** | 15.0 ± 1.57 | 3.08 ± 1.57''' |
| 48 hr | 197 ± 12.7 | 18.4 ± 4.32 | 62.0 ± 11.5** | 14.5 ± 2.66 | 2.81 ± 0.93''' |
| 72 hr | 197 ± 22.3 | 7.95 ± 3.80 | 69.1 ± 10.3** | 14.9 ± 3.33 | 2.87 ± 0.70''' |

TABLE 19-continued

Effect of 5-Fu and Oxaliplatin Combination with Elemene in Sequential Administration on Colon Cancer Cells HCT-15 (n = 8)

| Time | IC50 (µg/ml) | | | | |
|---|---|---|---|---|---|
| | Elemene alone | 5-Fu alone | 5-Fu + Elemene (160 µg/ml) | Oxaliplatin alone | Oxaliplatin + Elemene (160 µg/ml) |
| 4 hr/24 hr | 214 ± 15.8 | 80.0 ± 13.6 | 78.2 ± 24.6 | 22.0 ± 7.66 | 4.51 ± 1.45'''' |
| 4 hr/24 hr × 2 | 199 ± 11.5 | 40.0 ± 7.01 | 38.8 ± 12.2 | 16.4 ± 4.64 | 3.64 ± 1.16'''' |
| 4 hr/24 hr × 3 | 165 ± 23.0 | 28.4 ± 7.62 | 25.5 ± 5.64 | 11.8 ± 3.69 | 2.33 ± 1.23'''' |

Compared with 5-Fu alone *p < 0.05; **p < 0.01
Compared with oxaliplatin alone ''p < 0.05, '''p < 0.01

TABLE 20

Effect of 5-Fu and Oxaliplatin Combination with Elemene in Sequential Administration on Colon Cancer Cells Caco-2 (n = 8)

| Time | IC50 (µg/ml) | | | | |
|---|---|---|---|---|---|
| | Elemene alone | 5-Fu alone | 5-Fu + Elemene (100 µg/ml) | Oxaliplatin alone | Oxaliplatin + Elemene (100 µg/ml) |
| 4 hr | 171 ± 16.0 | 189 ± 27.1 | 45.4 ± 13.2** | 139 ± 19.1 | 86.1 ± 15.0'''' |
| 8 hr | 167 ± 32.9 | 102 ± 13.0 | 23.8 ± 6.93** | 132 ± 13.0 | 75.0 ± 9.85'''' |
| 12 hr | 104 ± 10.7 | 42.5 ± 9.84 | 9.81 ± 3.47** | 40.0 ± 17.4 | 4.62 ± 0.94'''' |
| 24 hr | 107 ± 6.00 | 23.9 ± 4.37 | 7.68 ± 2.74** | 26.3 ± 7.02 | 4.22 ± 1.63'''' |
| 48 hr | 91.0 ± 7.51 | 18.3 ± 2.83 | 4.80 ± 1.47** | 25.0 ± 6.08 | 2.62 ± 0.79'''' |
| 72 hr | 89.1 ± 9.08 | 12.6 ± 2.07 | 3.1 ± 2.76** | 9.20 ± 5.30 | 1.9 ± 0.23'''' |
| 4 hr/24 hr | 108 ± 2.55 | 28.8 ± 9.87 | 5.55 ± 0.85** | 37.5 ± 4.01 | 20.9 ± 2.20'''' |
| 4 hr/24 hr × 2 | 91.0 ± 7.55 | 17.0 ± 3.29 | 4.33 ± 1.26** | 19.5 ± 4.82 | 5.14 ± 1.41'''' |
| 4 hr/24 hr × 3 | 81.1 ± 10.3 | 13.8 ± 2.27 | 3.03 ± 1.21** | 9.11 ± 1.69 | 3.60 ± 0.65'''' |

Compared with 5-Fu alone *p < 0.05; **p < 0.01
Compared with oxaliplatin alone ''p < 0.05, '''p < 0.01

TABLE 21

Effect of 5-Fu and Oxaliplatin Combination with Elemene in Sequential Administration on Colon Cancer Cells Colo 205 (n = 8)

| Time | IC50 (µg/ml) | | | | |
|---|---|---|---|---|---|
| | Elemene alone | 5-Fu alone | 5-Fu + Elemene (80 µg/ml) | Oxaliplatin alone | Oxaliplatin + Elemene (80 µg/ml) |
| 4 hr | 144 ± 10.4 | 117 ± 9.02 | 41.1 ± 4.94** | 166 ± 7.51 | 75.8 ± 11.6'''' |
| 8 hr | 116 ± 4.00 | 91.3 ± 5.62 | 24.1 ± 2.66** | 124 ± 13.1 | 62.8 ± 8.01'''' |
| 12 hr | 110 ± 9.51 | 36.7 ± 4.66 | 13.9 ± 5.28** | 69.7 ± 12.7 | 37.6 ± 7.67'''' |
| 24 hr | 83.0 ± 13.7 | 21.1 ± 6.06 | 9.87 ± 4.48** | 25.2 ± 7.85 | 14.3 ± 6.68'''' |
| 48 hr | 75.3 ± 5.04 | 13.2 ± 1.44 | 6.93 ± 1.33** | 20.4 ± 2.14 | 10.6 ± 3.22'''' |
| 72 hr | 77.7 ± 14.2 | 11.0 ± 1.60 | 7.77 ± 4.82** | 13.4 ± 2.42 | 7.51 ± 1.83'''' |
| 4 hr/24 hr | 96.3 ± 11.1 | 34.6 ± 4.76 | 11.7 ± 0.98** | 29.5 ± 7.05 | 10.2 ± 2.15'''' |
| 4 hr/24 hr × 2 | 82.3 ± 7.11 | 26.3 ± 5.34 | 5.93 ± 1.99** | 21.8 ± 1.06 | 5.40 ± 1.15'''' |
| 4 hr/24 hr × 3 | 56.7 ± 12.6 | 11.6 ± 4.13 | 5.53 ± 2.03** | 9.90 ± 1.01 | 4.62 ± 0.99'''' |

Compared with 5-Fu alone *p < 0.05; **p < 0.01
Compared with oxaliplatin alone ''p < 0.05, '''p < 0.01

I claim:

1. A cytotoxic compound selected from the group consisting of (R)-2-((1R,3S,4S)-3-isopropenyl-4-methyl-4-vinyl-cyclohexyl)-propane-1,2-diol, (S)-2-((1R,3S,4S)-3-isopropenyl-4-methyl-4-vinyl-cyclohexyl)-propane-1,2-diol, and 1-((1R,3S,4S)-3-isopropenyl-4-methyl-4-vinyl-cyclohexyl)-ethanone.

2. A method for reducing the normal dosage of a chemotherapeutic agent given to a patient in need thereof for the treatment of a cancer without substantially reducing the effectiveness of said agent, said agent selected from the group consisting essentially of cisplatin, paclitaxel, docetaxel and fluorouracil (5-FU), said method comprising the steps of administering a therapeutically effective reduced dosage of said agent, and concurrently or sequentially administering an effective amount of (−)-beta-elemene.

3. The method of claim 2 wherein the cancer is selected from the group consisting essentially of brain cancer, lung cancer, ovarian cancer, bladder cancer, cervical cancer, colon cancer, breast cancer and prostate cancer.

4. A method for reducing the side effect(s) in a patient requiring a treatment for a tumor, said method comprising administering to said patient a reduced effective amount of a known active substance having antitumor effect selected from the group consisting essentially of cisplatin, paclitaxel, docetaxel and fluorouracil (5-FU), and an effective amount of (−)-beta-elemene, wherein said tumor is sensitive to said substance and wherein the administration of the (−)-beta-elemene reduces the side effects(s) experienced by said patient.

5. The method of claim 4 wherein the tumor is derived from a cancer selected from the group consisting essentially of brain cancer, lung cancer, ovarian cancer, bladder cancer, cervical cancer, colon cancer, breast cancer and prostate cancer.

6. A method for reducing the toxicity associated with a known active substance having antitumor effect selected from the group consisting essentially of cisplatin, paclitaxel, docetaxel and fluorouracil (5-FU), the method comprising concurrently or sequentially administering to a patient in need of such antitumor effect an effective amount of (−)-beta-elemene and a substantially reduced amount of said substance when compared with the effective amount of said substance administered without (−)-beta-elemene.

7. The method of claim 6 wherein the antitumor effect is against a tumor caused by a cancer selected from the group consisting essentially of brain cancer, lung cancer, ovarian cancer, bladder cancer, cervical cancer, colon cancer, breast cancer and prostate cancer.

8. In a method for minimizing either the individual or cumulative dose of a neoplastic agent used in the treatment of a patient suffering from a cancer that exhibits a dose dependent response to said agent, said agent selected from the group consisting essentially of cisplatin, paclitaxel, docetaxel and fluorouracil (5-FU), the improvement comprising the administration of said agent and the concurrent administration of (−)-beta-elemene in an amount sufficient to permit the individual or cumulative dose of said agent to be minimized without substantially reducing the efficacy of said agent, whereby unacceptably severe side effects are also minimized.

9. The method of claim 8 wherein the cancer is selected from the group consisting essentially of brain cancer, lung cancer, ovarian cancer, bladder cancer, cervical cancer, colon cancer, breast cancer and prostate cancer.

10. A method for enhancing the efficacy of a chemotherapeutic agent given to a patient in need thereof for the treatment of a cancer, said agent selected from the group consisting essentially of cisplatin, paclitaxel, docetaxel and fluorouracil (5-FU), said method comprising administering said agent to said patient and concurrently or sequentially administering to said patient an effective amount of (−)-beta-elemene.

11. The method of claim 10 wherein the cancer is selected from the group consisting essentially of brain cancer, lung cancer, ovarian cancer, bladder cancer, cervical cancer, colon cancer, breast cancer and prostate cancer.

12. A pharmaceutical composition having antitumor activity with reduced side effect(s) comprising a therapeutically effective reduced amount of a known active substance having antitumor effect selected from the group consisting essentially of cisplatin, paclitaxel, docetaxel and fluorouracil (5-FU), and an effective amount of (−−)-beta-elemene, together with a pharmaceutically acceptable carrier.

13. The composition of claim 12 wherein the antitumor activity is against a tumor caused by a cancer selected from the group consisting essentially of brain cancer, lung cancer, ovarian cancer, bladder cancer, cervical cancer, colon cancer, breast cancer and prostate cancer.

14. A method of imaging a tumor, comprising administering to a patient having a tumor a diagnostically effective amount of a detectable agent that is (−)-beta-elemene fluoride labeled with radioactive fluorine.

15. The method of claim 14 wherein the tumor is caused by a cancer selected from the group consisting essentially of brain cancer, lung cancer, ovarian cancer, bladder cancer, cervical cancer, colon cancer, breast cancer and prostate cancer.

16. A method for performing a diagnostic procedure to detect or image a tumor or for performing a therapeutic procedure on a tumor, the method comprising administering to a patient an effective amount of fluorine-labeled (−)-beta-elemene fluoride, and performing the diagnostic or therapeutic procedure.

17. The method of claim 16 wherein the tumor is caused by a cancer selected from the group consisting essentially of brain cancer, lung cancer, ovarian cancer, bladder cancer, cervical cancer, colon cancer, breast cancer and prostate cancer.

18. An imaging agent for imaging of a tumor site which comprises radioactive fluorine-labeled (−)-beta-elemene fluoride.

* * * * *